US009285575B2

(12) United States Patent
Xie et al.

(10) Patent No.: US 9,285,575 B2
(45) Date of Patent: Mar. 15, 2016

(54) SYSTEMS AND METHODS FOR SELECTIVE DETECTION AND IMAGING IN COHERENT RAMAN MICROSCOPY BY SPECTRAL EXCITATION SHAPING

(75) Inventors: Xiaoliang Sunney Xie, Lexington, MA (US); Christian Freudiger, Boston, MA (US); Wei Min, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 1047 days.

(21) Appl. No.: 12/690,579

(22) Filed: Jan. 20, 2010

(65) Prior Publication Data
US 2010/0188496 A1    Jul. 29, 2010

Related U.S. Application Data

(60) Provisional application No. 61/147,190, filed on Jan. 26, 2009.

(51) Int. Cl.
*G02B 21/00*    (2006.01)
*G01J 3/10*    (2006.01)
(Continued)

(52) U.S. Cl.
CPC .............. *G02B 21/002* (2013.01); *G01J 3/10* (2013.01); *G01J 3/44* (2013.01); *G01N 21/65* (2013.01);
(Continued)

(58) Field of Classification Search
None
See application file for complete search history.

(56) References Cited

U.S. PATENT DOCUMENTS 6,078,389 A    6/2000   Zetter
6,108,081 A    8/2000   Holtom et al.
(Continued)

FOREIGN PATENT DOCUMENTS

JP    2006516730 A    7/2006
WO    2004068126 A1    8/2004
(Continued)

OTHER PUBLICATIONS

Ploetz et al, Femtosecond Stimulated Raman Microsope, Apr. 12, 2007, Lasers and Optics, vol. 87, No. 3, pp. 389-393.*
(Continued)

*Primary Examiner* — Mehrdad Dastouri
*Assistant Examiner* — James M Anderson, II
(74) *Attorney, Agent, or Firm* — Gesmer Updegrove LLP

(57) ABSTRACT

A microscopy imaging system is disclosed that includes a light source system, a spectral shaper, a modulator system, an optics system, an optical detector and a processor. The light source system is for providing a first train of pulses and a second train of pulses. The spectral shaper is for spectrally modifying an optical property of at least some frequency components of the broadband range of frequency components such that the broadband range of frequency components is shaped producing a shaped first train of pulses to specifically probe a spectral feature of interest from a sample, and to reduce information from features that are not of interest from the sample. The modulator system is for modulating a property of at least one of the shaped first train of pulses and the second train of pulses at a modulation frequency. The optical detector is for detecting an integrated intensity of substantially all optical frequency components of a train of pulses of interest transmitted or reflected through the common focal volume. The processor is for detecting a modulation at the modulation frequency of the integrated intensity of substantially all of the optical frequency components of the train of pulses of interest due to the non-linear interaction of the shaped first train of pulses with the second train of pulses as modulated in the common focal volume, and for providing an output signal for a pixel of an image for the microscopy imaging system.

31 Claims, 16 Drawing Sheets

(51) Int. Cl.
*G01J 3/44* (2006.01)
*G01N 21/65* (2006.01)
*G02B 21/08* (2006.01)
*G01J 3/12* (2006.01)

(52) U.S. Cl.
CPC ....... *G02B 21/082* (2013.01); *G01J 2003/1282* (2013.01); *G01N 2021/653* (2013.01); *G01N 2021/655* (2013.01); *G01N 2201/0675* (2013.01)

(56) References Cited

U.S. PATENT DOCUMENTS

| | | | |
|---|---|---|---|
| 6,798,507 | B2 | 9/2004 | Xie et al. |
| 6,809,814 | B2 | 10/2004 | Xie et al. |
| 7,092,086 | B2 * | 8/2006 | Knebel ............ 356/301 |
| 7,266,401 | B2 * | 9/2007 | Lipson ............ 600/316 |
| 7,277,178 | B2 * | 10/2007 | Shpantzer et al. ............ 356/451 |
| 7,352,458 | B2 * | 4/2008 | Xie et al. ............ 356/301 |
| 7,821,633 | B2 * | 10/2010 | Jalali et al. ............ 356/301 |
| 2008/0088907 | A1 * | 4/2008 | Wolleschensky ............ 359/256 |
| 2009/0296744 | A1 * | 12/2009 | Dantus et al. ............ 372/5 |
| 2010/0046039 | A1 | 2/2010 | Xie et al. |

FOREIGN PATENT DOCUMENTS

| | | |
|---|---|---|
| WO | 2007112449 A2 | 10/2007 |
| WO | WO 2007112449 A2 * | 10/2007 |

OTHER PUBLICATIONS

Boysworth et al., "Generalization of multivariate optical computations as a method for improving the speed and precision of spectroscopic analyses", J. Chemometrics, Jan. 3, 2008. vol. 22, pp. 355-365.

Cheng et al., "Multiplex coherent anti-stokes raman scattering microspectroscopy and study of lipid vesicles", J. Phys. Chem. B. Jul. 19, 2002. vol. 106, pp. 8493-8498.

Freudiger et al., "Label-free biomedical imaging with high sensitivity by stimulated raman scattering microscopy", Science. Dec. 19, 2008. vol. 322, pp. 1857-1861.

Ganikhanov et al., "High-sensitivity vibrational imaging with frequency modulation coherent anti-stokes raman scattering (FM CARS) microscopy", Optics Letters. Jun. 15, 2006. vol. 31, No. 12, pp. 1872-1874.

Ploetz et al., "Femtosecond stimulated raman microscopy", Applied Physics B Laser and Optics. Apr. 12, 2007. vol. 87, pp. 389-393.

Uzunbajakava et al., "Low-cost spectroscopy with a variable multivariate optical element", Analytical Chemistry. Oct. 16, 2006. vol. 78, No. 20, pp. 7302-7308.

Zumbusch et al., "Three-dimensional vibrational imaging by coherent anti-stokes raman scattering", Physical Review Letters. May 17, 1999. vol. 82, No. 20, pp. 4142-4145.

Freudiger et al., "Label-Free Biomedical Imaging with High Sensitivity by Stimulated Raman Scattering Microscopy" Science, vol. 322, Dec. 19, 2008, pp. 1857-1861.

Shim et al., "Generation of narrow-bandwidth picosecond visible pulses from broadband femtosecond pulse for femtosecond stimulated Raman" Applied Physics Letters 89, 2006, pp. 121124-1-121124-3.

Lim et al., "Single pulse interferomteric coherent anti-Stokes Raman scattering (CARS)" Jan. 1, 2007, Proc. of SPIE, vol. 6442, pp. 644205-1-644205-10.

Ozeki et al., "Analysis and experimental assessment of the sensitivity of stimulated Raman scattering microscopy" Mar. 2, 2009, Optics Express, vol. 17, No. 5, pp. 3651-3658.

Fischer et al., "Enhancing Two-Color Absorption, Self-Phase Modulation and Raman Microscopy Signatures in Tissue with Femtosecond Laser Pulse Shaping" Feb. 12, 2009, Proc. of Spie, vol. 7183, pp. 71830V-1-71830V-11.

The EP Extended Search Report issued in connection with European Application No. 10151529.4 mailed on Feb. 14, 2013.

The EP Communication issued in connection with European Application No. 10151529.4 mailed on Mar. 25, 2013.

The EP Communication mailed on Apr. 7, 2014, correlating to corresponding EP Application No. 10151529.4-1554.

The Intent to Grant mailed on Apr. 30, 2015, correlating to corresponding EP Application No. 10151529.4-1554.

Notice of Rejection issued by the Japanese Patent Office on Mar. 27, 2012 in connection with related Japanese Patent Application No. 2010-013744 and partial English translation thereof, 9 pages.

* cited by examiner

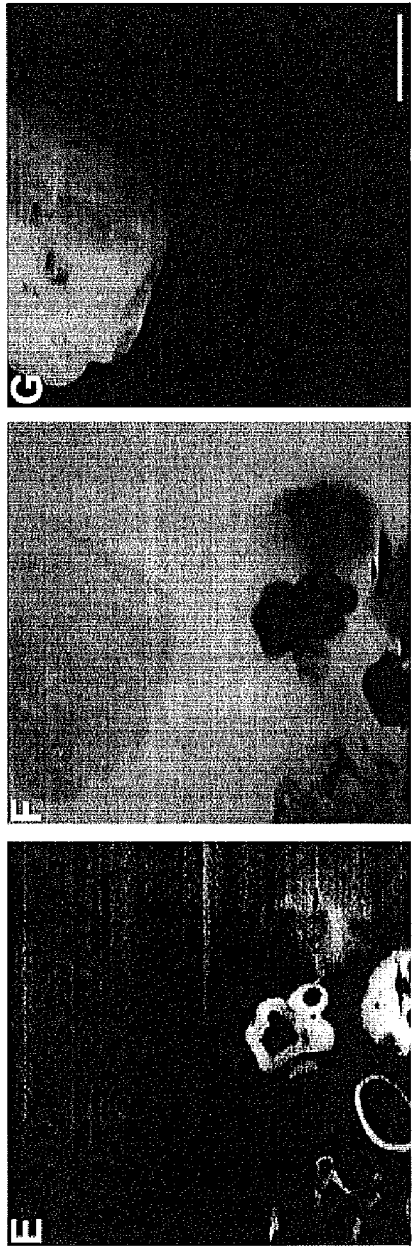

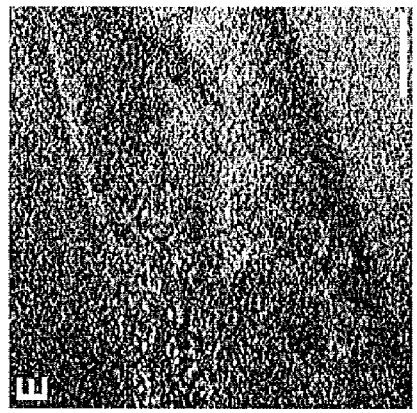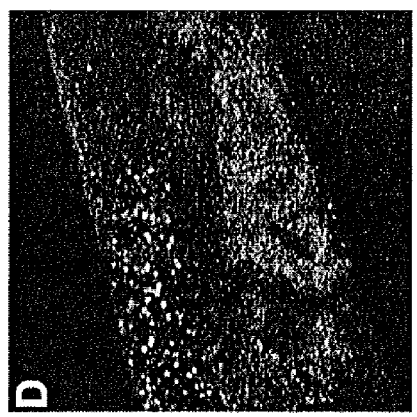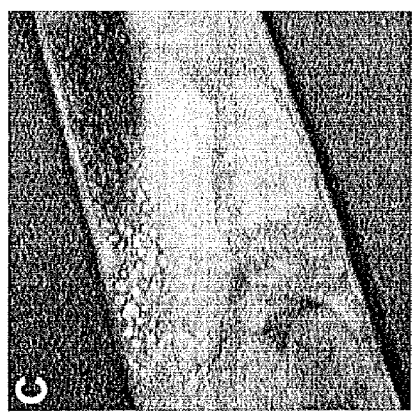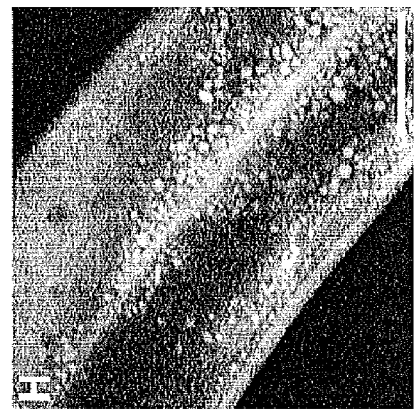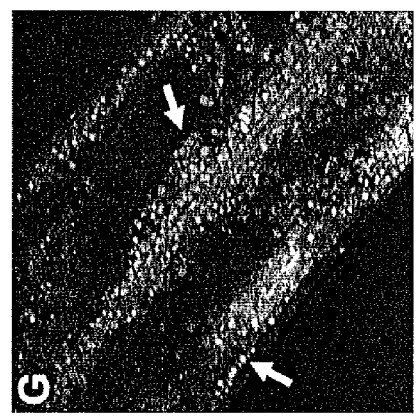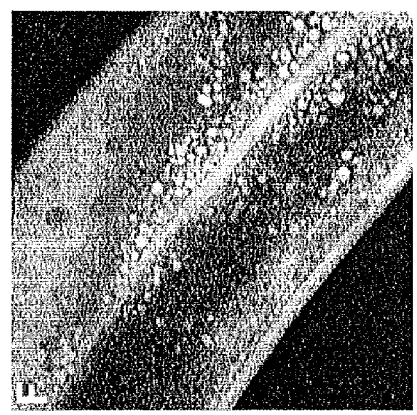

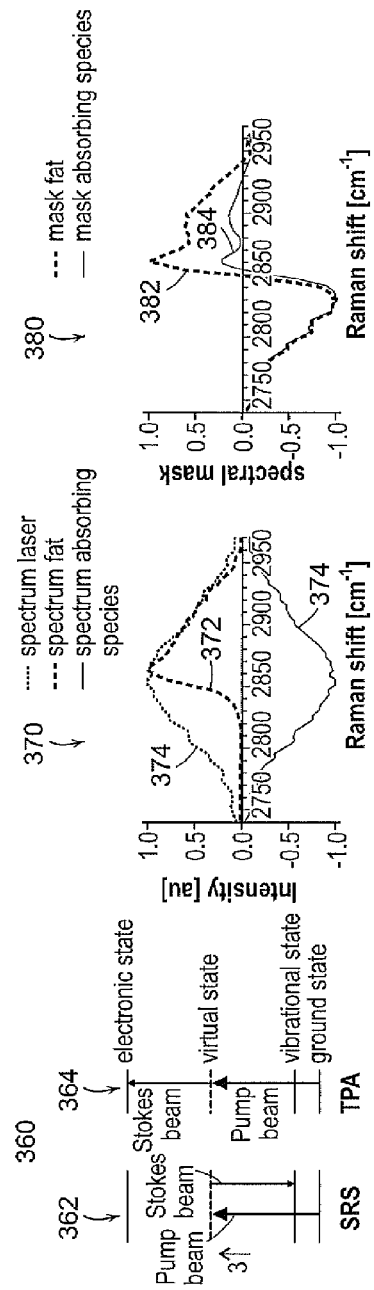
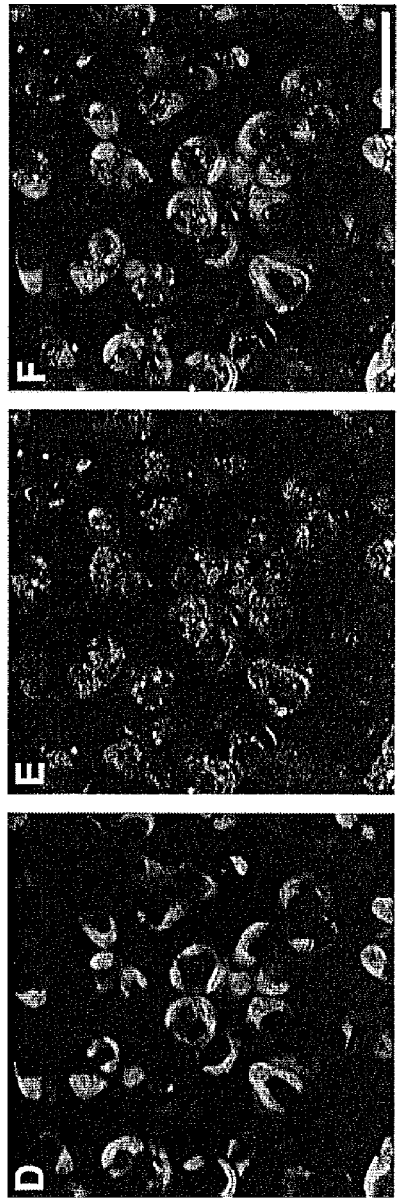

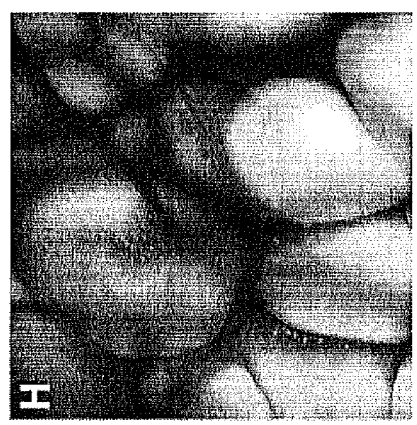
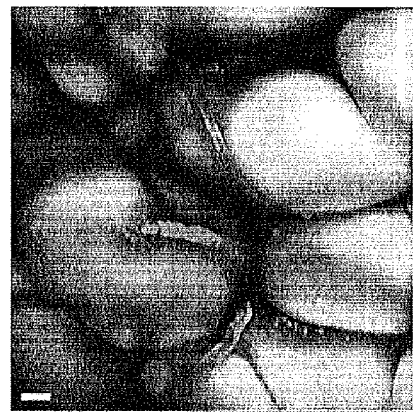
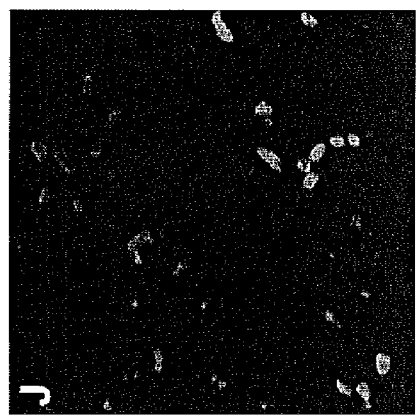
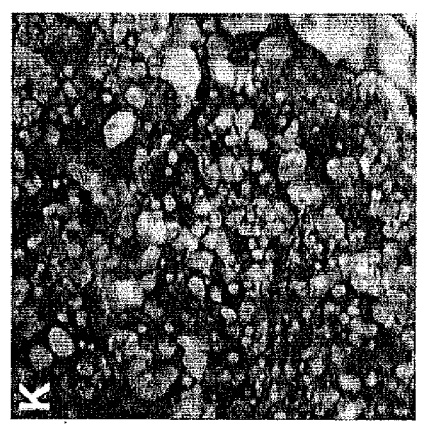
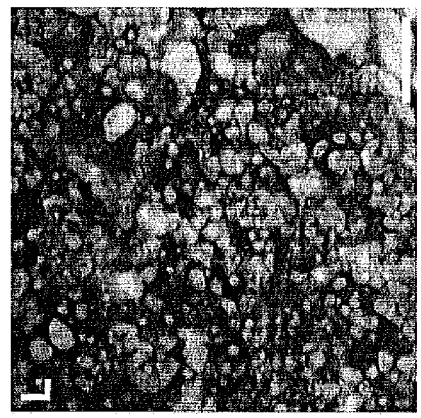

SYSTEMS AND METHODS FOR SELECTIVE DETECTION AND IMAGING IN COHERENT RAMAN MICROSCOPY BY SPECTRAL EXCITATION SHAPING

PRIORITY

The present application claims priority to U.S. Provisional Patent Application Ser. No. 61/147,190 filed Jan. 26, 2009.

This invention was made with government support under DE-FG02-07ER15875 awarded by the U.S. Department of Energy, OD000277 awarded by the National Institutes of Health, and 0649892 awarded by the National Science Foundation. The government has certain rights to the invention.

BACKGROUND

The invention generally relates to vibrational microscopy and imaging systems, and relates in particular to vibrational imaging systems employing coherent Raman scattering.

Conventional vibrational imaging techniques include, for example, infrared microscopy, spontaneous Raman microscopy, and coherent anti-Stokes Raman scattering microscopy.

Infrared microscopy, which generally involves directly measuring the absorption of vibrational excited states in a sample, is limited by poor spatial resolution due to the long wavelength of infrared light, as well as by a low penetration depth due to a strong infrared light absorption by the water in biological samples.

Raman microscopy records the spontaneous inelastic Raman scattering upon a single (ultraviolet, visible or near infrared) continuous wave (CW) laser excitation. Raman microscopy has improved optical resolution and penetration depth as compared to infrared microscopy, but the sensitivity of Raman microscopy is rather poor because of the very low spontaneous Raman scattering efficiency; a Raman scattering cross section is typically on the order of $10^{-30}$ cm$^2$. This results in long averaging times per image, which limits the biomedical applications of Raman microscopy.

Coherent anti-Stokes Raman (CARS) microscopy systems provide increased scattering signal from a sample due to coherent excitation. CARS microscopy systems use two pulsed excitation laser beams (pump and Stokes beams) with a frequency difference that matches the molecular vibration frequency of the chemical species to be imaged. As a result of interaction of the chemical species to be imaged with the difference frequency between the pump and Stokes beams, new illumination is generated at the sample at the anti-Stokes frequency, which is detected as the output signal in CARS microscopy. Imaging speeds up to video-rate have been achieved from highly resonant samples.

The CARS process, however, also excites a high level of background from the vibrationally non-resonant specimen. Such a non-resonant background not only distorts the CARS spectrum of the resonant signal from dilute samples but also carries the laser noise, significantly limiting the application of CARS microscopy on both spectroscopy and sensitivity perspectives. Various techniques have been developed to suppress this background, as disclosed, for example, in U.S. Pat. Nos. 6,798,507 and 6,809,814, but such systems each provides an anti-Stokes signal that is at least somewhat reduced by the background suppression.

Moreover, the specificity of the anti-Stokes signals for certain target species is limited because many chemical species may have a vibrational response at multiple frequencies. For example, FIG. 1 shows at 10 a Raman spectrum for the bioactive molecule adenosine triphosphate (ATP), the chemical formula for which is shown at 12 in FIG. 2. Note that because ATP has many different types of atomic bonds, it has several Raman active peaks that together provide a characteristic vibrational signature of the molecules.

The specificity is limited since many different chemical species (e.g., one target species and one non-target species) may have some of the same bonds (e.g., O—H) that provide the same vibrational response at the anti-Stokes frequency to the excitation illumination, making distinguishing between the two chemical species difficult or impossible based on a single anti-Stokes frequency.

Spectroscopy imaging systems have also been developed in which a broadband pulse is dispersed onto a multi-channel detector (photodiode-array or CCD) after passing through the focus, such that all spectral components can be individually detected. For example, synchronized broadband and narrowband pulse trains may be provided from mode-locked lasers. The combined pulse trains are provided to a laser-scanning microscope, and the nonlinear sample interaction occurs in the focus of the laser-scanning microscope. Output radiation is then provided to a dispersion device such as a grating or prism and then onto a multi-channel detector such as a photodiode array of a CCD after passing through the focus. Because of the use a spectrometer, images can only be achieved by slow stage scanning or low-throughput de-scanned detectors.

Such an approach is also difficult to unify with the high sensitivity detection schemes that require processing electronics such as a lock-in amplifier because every spectral component would need its own electronics. Furthermore spectroscopy is difficult to combine with laser-scanning microscopy because after passing through the sample the beam can move on the spectrometer and thus hinder the spectrum acquisition.

There is a need, therefore, for a microscopy imaging system that provides improved sensitivity and specificity. There is a further need for a microscopy imaging system that probes multiple Raman vibrations simultaneously to extract a spectral fingerprint that is free from spectral interference from other atomic bonds within a sample.

SUMMARY

In accordance with an embodiment, the invention provides a microscopy imaging system that includes a light source system, a spectral shaper, a modulator system, an optics system, an optical detector and a processor. The light source system is for providing a first train of pulses including a first broadband range of frequency components, and a second train of pulses including a second optical frequency such that a set of differences between the first broadband range of frequency components and the second optical frequency is resonant with a set of vibrational frequencies of a sample in the focal volume. The second train of pulses is synchronized with the first train of pulses. The spectral shaper is for spectrally modifying an optical property of at least some frequency components of the broadband range of frequency components such that the broadband range of frequency components is shaped producing a shaped first train of pulses to specifically probe a spectral feature of interest from a sample, and to reduce information from features that are not of interest from the sample. The modulator system is for modulating a property of at least one of the shaped first train of pulses and the second train of pulses at a modulation frequency to provide a modulated train of pulses. The optics system is for directing and focusing the shaped first train of pulses and the second train of pulses as modulated toward a common focal volume. The optical detector is for detecting an integrated intensity of substantially all optical frequency components of a train of pulses of interest transmitted or reflected through the common focal volume. The processor is for detecting a modulation at the modulation frequency of the integrated intensity of substantially all of the optical frequency components of the train of pulses of interest due to the non-linear interaction of the shaped first train of pulses with the second train of pulses as modulated in the common focal volume, and for providing an output signal for a pixel of an image for the microscopy imaging system.

In accordance with another embodiment, the system provides a method of performing microscopy imaging using frequency modulation. The method includes the steeps of providing a first train of pulses at including a first broadband range of optical frequency components; providing a second train of pulses including a second optical frequency such that a set of differences between the first broadband range of frequency components and the second optical frequency is resonant with a set of vibrational frequencies of a sample in the focal volume, wherein the second train of pulses is synchronized with the first train of pulses; and spectrally modifying an optical property of at least some frequency components of the first broadband range of frequency components to provide a shaped first train of pulses that is shaped to specifically probe a spectral feature of interest from a sample, and to reduce information from features that are not of interest from the sample. The method further includes the steps of modulating an optical property of one of the shaped first train of pulses and the second train of pulses at a modulation frequency to provide a modulated train of pulses and providing the other of the shaped first train of pulses and the second train of pulses as a non-modulated train of pulses; directing and focusing the modulated train of pulses and the non-modulated train of pulses toward a common focal volume; detecting an integrated intensity of substantially all optical frequency components of the other of the modulated train of pulses and the non-modulated train of pulses transmitted or reflected through the common focal volume by blocking the modulated train of pulses; detecting a modulation at the modulation frequency of the integrated intensity of substantially all of the optical frequency components of the non-modulated train of pulses due to the non-linear interaction of the modulated train of pulses with the non-modulated train of pulses in the common focal volume; and providing the detected modulation as the signal for a pixel of an image for a microscopy imaging system.

BRIEF DESCRIPTION OF THE DRAWINGS

The following description may be further understood with reference to the accompanying drawings in which:

FIGS. 18A-18G show illustrative graphical data and images associated with spectral SRS imaging obtained using a system in accordance with an embodiment of the invention;

FIGS. 19A-19H show illustrative graphical data and images in connection with lipid storage in *Caenorhabditis Elegans* obtained using a system in accordance with an embodiment of the invention; and FIGS. 20A-20L show illustrative graphical data and images in connection with label-free microscopy of absorbing samples obtained using a system in accordance with an embodiment of the invention.

The drawings are shown for illustrative purposes only.

DETAILED DESCRIPTION

In accordance with certain embodiments, the invention provides excitation illumination that is spectrally and temporally designed to probe specific species, and in further embodiments the excitation illumination probes multiple chemical species simultaneously. In accordance with some embodiments, the excitation illumination systems may be employed with stimulated Raman scattering microscopy systems.

The present invention, involves, in part, performing excitation spectroscopy instead of detection spectroscopy for Stimulated Raman Scattering (SRS) and Coherent Anti-Stokes Raman Scattering (CARS) microscopy, as well as two-color two-photon absorption and photothermal imaging, in order to overcome the above cited shortcomings of prior art systems. Instead of providing a complete broadband spectrum as the broadband excitation beam only selected frequency components of one excitation mask may be detected with a single detector, and the SRS may be extracted with a high-frequency detection scheme. Spectral shaping has the advantage that subsequent excitation masks may be applied without having to change the laser. Different masks may be applied after each imaging frame or on a pixel-by-pixel basis.

Figure 3:
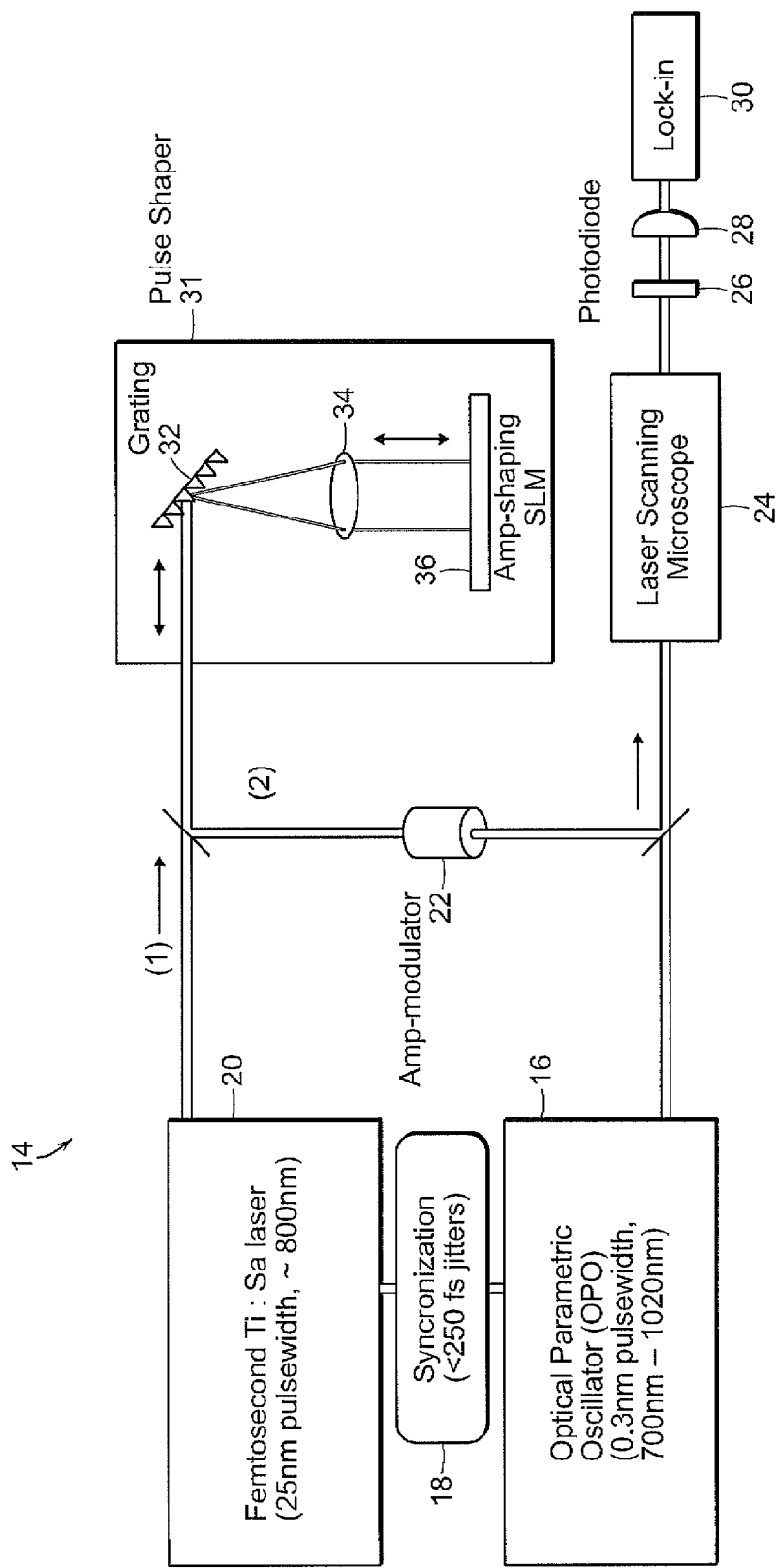
FIG. 3 shows an illustrative diagrammatic view of a multiplex excitation microscopy system in accordance with an embodiment of the invention.

FIG. 3 shows a possible setup of an SRG microscope in which excitation spectroscopy may be performed by pulse-shaping the broadband beam. The system 14 includes a picoseconds (narrowband) optical parametric oscillator 16, a synchronization unit 18, a femtosecond (broadband) Ti:SA laser 20, and an amplitude modulator 22. The pump-beam is modulated at frequency $f$ (>1 MHz) with the amplitude modulator 22, and the pump and Stokes beams are provided to a laser-scanning microscope 24. The pump and Stokes beams that are transmitted or reflected through the focal volume are filtered by the optical filter 26 to block the modulated pump beam and the filtered Stokes beam 30 is detected by a photodetector such as a photodiode 28. In various embodiments, the first train of pulses may be femtosecond pulses and the second train of pulses may be picosecond pulses or femtosecond pulses.

The modulation of the detected intensity of the Stokes beam due to the nonlinear interaction with the sample is extracted with an electronic processing unit such as a lock-in amplifier. Excitation spectroscopy is performed by shaping the broadband pulse by an amplitude or polarization pulse shaper 31 that consists of a dispersive element 32 that disperses the individual frequency components of the broadband beam onto the different elements of a multiplex amplitude or polarization shaper such as a spatial light modulator 36. Such a device can work in reflection mode (as shown) or in transmission mode. Typically, a lens 34 is positioned in a way to refocus the reflected beam such that an un-chirped, spectrally homogenous beam is provided to the spatial light modulator 36. In various embodiments, the settings on the pulse shaper 31 may also be changed or modulated during imaging to provide either a modulation of the pulse train or to provide different sets of pulse shapes for probing multiple species within a sample.

In line with the high-frequency modulation scheme presented above and necessary for high-sensitivity SRS detection, amplitude modulation is performed with an additional electro-optical or acoustic-optical modulator, for example in the set-up shown in FIG. 3. Alternatively, it is possible that pulse-shaping of the broadband beam and amplitude modulation for high-frequency detection may be performed by the same device such as an acousto-optic tunable filter (AOTF). Pump and Stokes beam may be combined with a dichroic beam-combiner. If the pump-beam is modulated for stimulated Raman gain (SRG) as discussed further below, all frequency components of the Stokes beam are collected with a single photodiode as described above and the SRG for a particular excitation pattern is extracted with electronic processing systems such as a lock-in detector to provide the pixel of an image.

Figure 4:
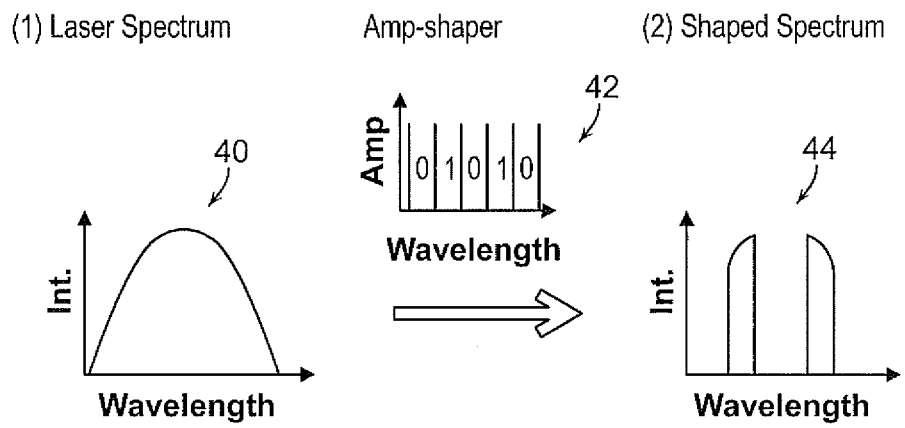
FIG. 4 shows an illustrative diagrammatic view of the generation of an excitation mask in accordance with an embodiment of the invention.

FIG. 4 shows how such an excitation mask may be generated from a broadband laser spectra 40 and a pulse shaper 42 that consists of a dispersive element (grating or prism) and a multiplex amplitude shaper (such as a spatial light modulator SLM or printed transmission/reflection mask) that can individually control the intensity of every frequency components of the broadband excitation pulse to provide a shaped train of pulses as shown at 44.

Such an approach can improve specificity by implementation of a background subtraction scheme for interfering species. Instead of illuminating the sample with one excitation mask, the signal for two masks is measured. A first mask 1 contains mainly the frequency components of the target molecule and a second mask 2 contains mainly the frequency components of interfering species. Because of the spectral interference of the target molecule with interfering or other species in certain applications, the signal for mask/can never be chosen to only contain contributions from the target species but will always excite signal from the interfering or other species. It is however, always possible to design the two excitation masks in a way, that the difference between the intensities for the two masks is independent of the concentration of the interfering or other species. In accordance with further embodiments, the two more species may be probed separately wherein for each probing information from the non-probed species is reduced.

The difference between the signal from mask 1 and mask 2 may either be taken on a pixel by pixel basis or an image with mask 1 and mask 2 may be taken first and the subtraction may be performed in the post-processing. The idea of this multivariate optical computation has been used for emission spectroscopy for spontaneous Raman scattering as shown in the prior art, but not for excitation spectroscopy in combination with high sensitivity detection in SRS or CARS.

In accordance with further embodiments, pulse shaping may be achieved using a multiplex electro-optic modulator, a multiplex electro-acoustic modulator, an acousto-optic tunable filter, or a Dazzler system as sold by Fastlite Société à responsabilité limitée of Saint-Aubin France. The broadband beam is not required to have all frequency components within a range present in the beam, but instead may be composed of a plurality of center frequency components, as long as sufficient frequency components are present in the broadband beam that may be shaped for probing a sample as desired. The spectral range of the broadband beam may be, for example, at least 15.0 nm, or at least 5.0 nm, or at least 1.0 nm, or even at least 0.5 nm in certain embodiments.

Figure 5A:
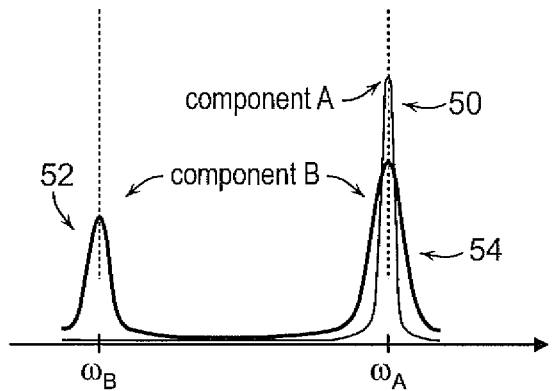
FIGS. 5A-5C show illustrative diagrammatic views of response signals from two components of a sample that may be interrogated in accordance with an embodiment of the invention.
Figure 5B:
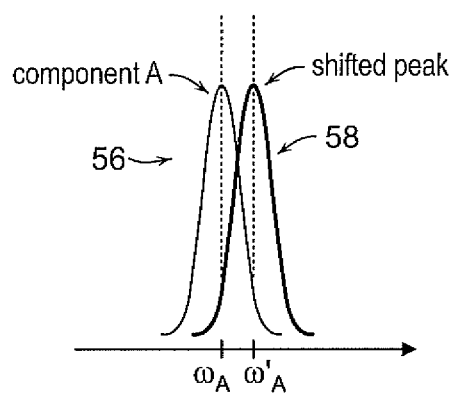
Figure 5C:
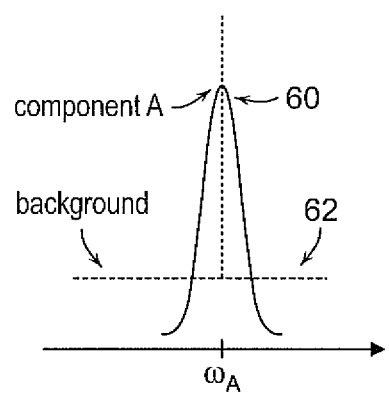

FIGS. 5A to 5C show three fundamental scenarios of possible spectral crosstalk between two species. In FIG. 5A the only strong peak of the target molecule component A at $\omega_A$ as shown at 50 overlaps with the spectrum of another species (component B in the sample) as shown at 52 and 54 that has a second peak at $\omega_B$. In this situation the first excitation mask is chosen such that it gives maximum signal for the peak at $\omega_A$, yielding the signal from component A and component B. The second excitation mask is chosen in a way that it removes the interfering signal from component B after subtracting the signal from the first mask and the second mask.

The masks may be designed in such a way, that the signal from the isolated peak of the interfering species is scaled in such a way that after subtraction this only leaves the pure signal from the target species, which is independent of the concentration of component B. FIG. 5B shows at 56 and 58 the case of a spectrally shifted target peak due to the chemical environment. In this situation the two excitation masks can be chosen in a way that the original peak from the un-shifted species does not contribute to the signal after subtraction (e.g., signal from the left half of the peak minus signal from the right half of the peak). In FIG. 5C the spectra from the target species as shown at 60 sits on top of a spectrally flat background as shown at 62. Such a background may arise from other nonlinear processes as Kerr-lensing and two-color two-photon absorption or a strongly broadened vibrational resonance in SRS and from the non-resonant background in CARS. The two masks can be chosen to maximize the signal from the peak and subtract the flat background.

Figure 6:
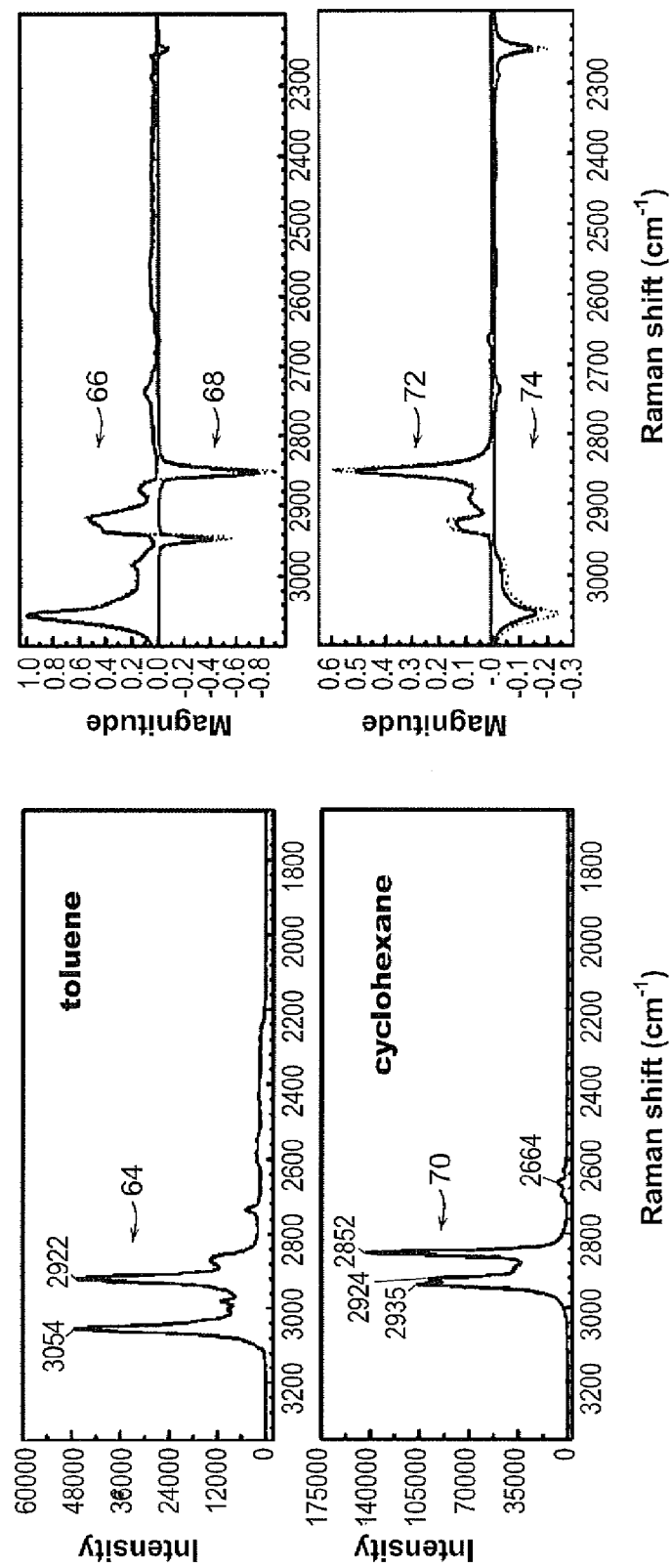
FIG. 6 shows illustrative graphical representations of Raman shift verses intensity and magnitude for toluene and cyclohexane.

FIG. 6 shows how the scenarios illustrated in FIGS. 5A-5C may be applied to more complex spectra and more than one interfering species. In particular, FIG. 6 shows at 64 the spectra for toluene, and shows at 66 the positive mask to probe for toluene, while 68 shows a negative mask to exclude an interfering species. FIG. 6 also shows at 70 the spectra for cyclohexane, and shows at 72 the positive mask to probe for cyclohexane, while 74 shows a negative mask to exclude an interfering species. This approach has been applied to emission spectroscopy and is known as 'multivariate optical calculation'. It is based on treating spectra as N dimensional vectors, where N is the number individual frequency components of the excitation pulse, and the applied masks as co-vectors.

It is also desirable to comprise a concrete implementation for fast switching between the two excitation masks for a pixel-by-pixel subtraction. Because laser noise occurs primarily at frequencies<1 MHz, the difference between the excitation masks needs to be taken at fast rates to achieve maximum sensitivity for the target molecule. The approach is based on polarization-shaping the broadband pulse (s-polarization corresponds to mask 1 and p-polarization corresponds do mask 2) and switching between the two polarization states, i.e., excitation masks, with an electro-optic modulator (Pockel cell). A similar approach may be used in an implementation of frequency modulation CARS.

Figure 7:
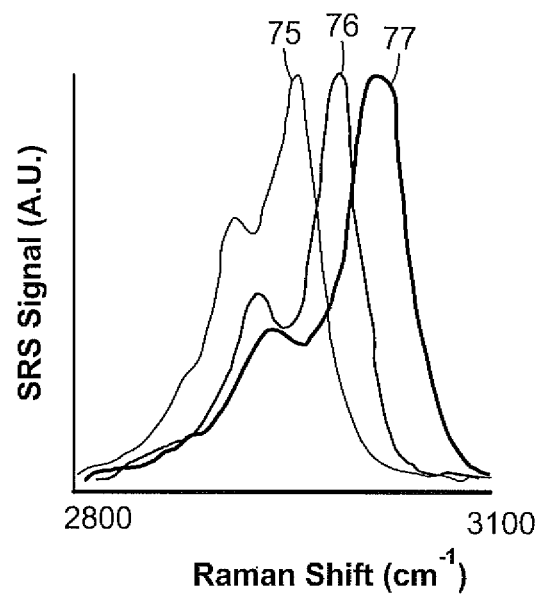
FIG. 7 shows an illustrative graphical representation of Raman shift verses stimulated Raman signal in a system in accordance with an embodiment of the invention.

A more complex scenario is shown in FIG. 7. Molecule A (shown at 75) is the analyte of interest, while elements B (shown at 76) and C (shown at 76) are the interfering or other species. Note that the corresponding known Raman spectra $\sigma(\Delta\omega)$ of A, B, and C are partially overlapping with each other as shown.

The objective is to design positive excitation spectral shapes. In a mixture of A, B and C with unknown concentrations c of each one, two positive excitation spectral shapes $I_+(\Delta\omega)$ and $I_-(\Delta\omega)$ (i.e. masks) may be designed such that the difference signal $\Delta S$ from these two excitation masks can selectively predict the concentration of molecule A without getting interference from molecules B and C.

For a given excitation spectral shape $I(\Delta\omega)$, the obtained absorption signal S will be described by the following $$S \propto \int I(\Delta\omega)[c_A\epsilon_A(\Delta\omega)+c_B\epsilon_B(\Delta\omega)+c_C\epsilon_C(\Delta\omega)]d\Delta\omega$$

For two excitation spectral shapes $I_+(\Delta\omega)$ and $I_-(\Delta\omega)$, the difference signal $\Delta S$ will be $$\Delta S \equiv S_+ - S_- \propto \int [I_+(\Delta\omega)-I_-(\Delta\omega)][c_A\epsilon_A(\Delta\omega)+c_B\epsilon_B(\Delta\omega)+c_C\epsilon_C(\Delta\omega)]d\Delta\omega$$

It is mathematically possible that we can design positive $I_+(\Delta\omega)$ and $I_-(\Delta\omega)$ functions such as their difference function satisfy the following orthogonal relations with the Raman spectra of all the interferent species:

$$\int [I_+(\Delta\omega)-I_-(\Delta\omega)]\epsilon_B(\Delta\omega)d\Delta\omega=0 \text{ and } \int[I_+(\Delta\omega)-I_-(\Delta\omega)]\epsilon_C(\Delta\omega)d\Delta\omega=0$$

Note that the Raman shift-dependent $I_+(\Delta\omega)-I_+(\Delta\omega)$ has both positive and negative values. As a result, we can simplify the quantity $$\int[I_+(\Delta\omega)-I_-(\Delta\omega)][c_A\epsilon_A(\Delta\omega)+c_B\epsilon_B(\Delta\omega)+c_C\epsilon_C(\Delta\omega)]d\Delta\omega=\int[I_+(\Delta\omega)-I_-(\Delta\omega)]c_A\epsilon_A(\Delta\omega)d\Delta\omega$$

The difference signal therefore, is only proportional to the concentration of molecule of interest:

$$\Delta S \equiv S_+ - S_- \propto c_A\int[I_+(\Delta\omega)-I_-(\Delta\omega)]\epsilon_A(\Delta\omega)d\Delta\omega$$

Figure 8:
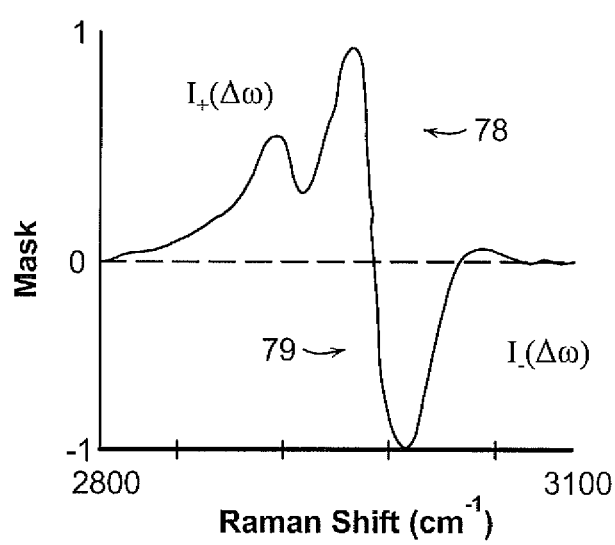
FIG. 8 shows an illustrative graphical representation of Raman shift verses mask selectivity in a system in accordance with an embodiment of the invention.

FIG. 8 shows a design for excitation spectral shapes using masks $I_+(\Delta\omega)$ (shown at 78) and $I_-(\Delta\omega)$ (shown at 79). The mask $I_+(\Delta\omega)$ 78 is designed to enhance imaging of the element of interest, while the mask $I_-(\Delta\omega)$ 79 is designed to reduce the imaging of interfering elements.

Because changing different components of excitation spectrum by pulse-shaping does not require the laser to change, fast switching speeds are possible allowing for spectra-temporal shaping of the excitation beams to encode the signal from different chemical species in time (or modulation phase and frequency) instead of optical frequency such that it can be detected with a single detector. This allows implementation of: 1) real-time detection of pure signal from target species free from the background signal of interfering species by the subtraction scheme of the two-masks as described above, and 2) simultaneous multicolor imaging with a single detector.

It is desirable to comprise a concrete implementation for fast switching between multiple excitation, masks, because laser noise occurs primarily at frequencies<1 MHz and different excitation masks need to be probed faster than the laser can change. The sample may also change in between frames (e.g., move), making a frame-by-frame acquisition of different mask impossible.

Technically there are many multiple technologies to achieve such fast spectral modulations, such as: 1) spectral modulation with a single device such as an electro-optic or acousto-optic modulator that allows the independent modulation of individual spectral component of the broadband excitation beam, and 2) a combination of a polarization pulse shaper, polarization modulator and polarization analyzer.

Systems of the invention may be employed with stimulated Raman scattering (SRS) microscopy systems as follows. Stimulated Raman scattering allows the detection of the vibrational signal with higher signal levels than spontaneous Raman scattering due to stimulated excitation of molecular vibrations and without exciting the non-resonant background signal of CARS microscopy. Spontaneous Raman spectra are thus preserved and the signal strength scales linearly with the concentration allowing for straight forward quantification. Forward- and reverse (epi)-detection is possible, as well as SRS endoscopy.

In a narrowband SRS microscopy, pump and Stokes-beam are used to excite the sample, just as in CARs microscopy. Instead of detecting the newly emitted light at the anti-Stokes frequency, intensity gain (stimulated Raman gain) at the pump frequency or intensity loss (stimulated Raman loss) at the Stokes frequency are detected. As the gain and loss are relatively small a high-frequency detection scheme is often required, in which the SRS signal is modulated at a known frequency that is higher than the laser noise and is extracted with an electronic detector such as a lock-in amplifier to provide the intensity of a pixel. The modulation may be frequency modulation, phase modulation or amplitude modulation.

In this narrowband approach to coherent Raman imaging (CARS and SRS microscopy) only a single molecular vibration can be imaged at a time. Thus only single color images can be produced (compared to imaging multiple species simultaneously) and detection is limited to chemical species that have an isolated vibration that does spectrally not interfere with other compounds in the sample. The present invention provides (in certain embodiments) methods and systems to allow coherent Raman imaging based on multiple Raman lines simultaneously.

For example, fast, label-free imaging of biological samples based on vibrational signatures of the target molecules is possible with SRS. High sensitivity (measurement of intensity changes $\Delta I/I<10^{-7}$) even with noisy lasers may be achieved by implementation of high-frequency (>1 MHz) signal modulation and phase sensitive detection with a lock-in amplifier, because laser noise primarily occurs at lower frequencies. For SRS imaging a single vibrational frequency is selected by tuning the frequency difference of the two-excitation lasers. The spatial distribution of the target molecule in the sample can be probed with a laser-scanning microscope by raster-scanning the laser-focus through the sample. Vibrational excitation spectra from a single point in the sample can be obtained by automated tuning of the excitation laser frequency. Excitation pulsed lasers (~5 ps) are useful that provide high peak intensities (favoring the nonlinear optical interaction at the low average intensity required for biomedical imaging) and provide high enough spectral resolution (~3 $cm^{-1}$) to time into selected vibrational bands even if the 'integrated intensity of substantially all the optical frequency components of the laser is collected.

Figures 9A, 9B:
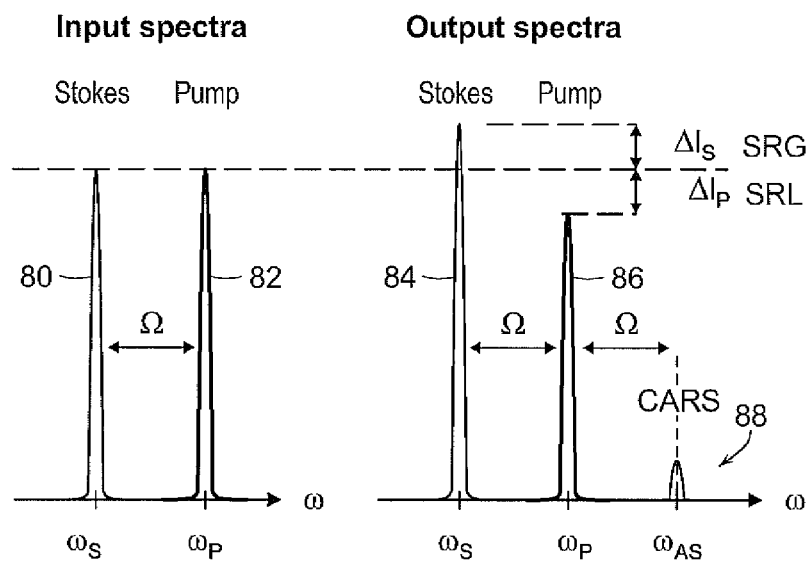
FIGS. 9A and 9B show illustrative diagrammatic representations of input and output spectra respectively for a stimulated Raman spectroscopy system in accordance with an embodiment of the invention.

In particular, a pump beam and a Stokes beam in a sample volume enhance a spontaneous Raman radiation signal. The center frequency of the Stokes beam and the center frequency of the pump beam are separated by an input spectra difference $\Omega$ as shown at 80 and 82 in FIG. 9A. As shown in FIG. 9B, SRS leads to an intensity increase in the Stokes beam (stimulated Raman gain or SRG) and an intensity decrease in the pump beam (stimulated Raman loss or SRL) as shown at 84 and 86. Also shown (not to scale) is the CARS signal 88 that is generated at the anti-Stokes frequency $\omega_{AS}$.

Figures 10A, 10B:
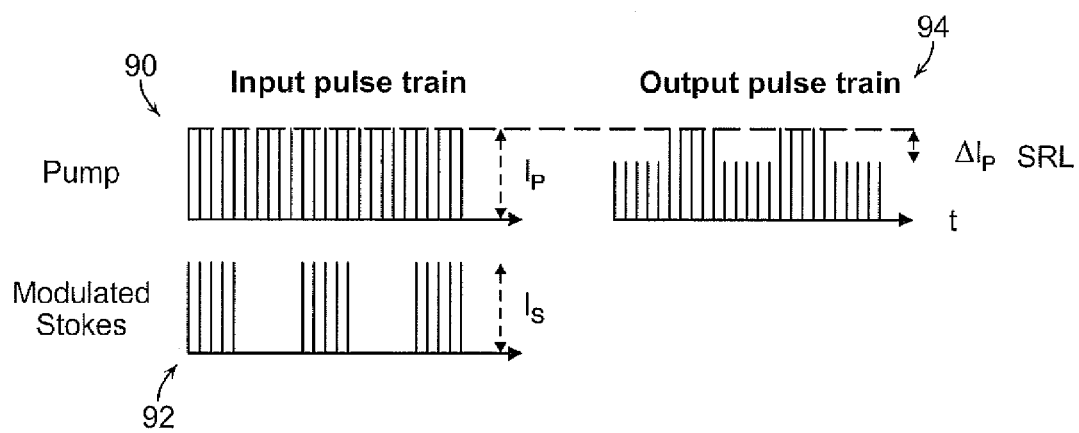
FIGS. 10A and 10B show illustrative diagrammatic representations of input and output pulse trains respectively for a stimulated Raman spectroscopy system in accordance with an embodiment of the invention.

FIGS. 10A and 10B illustrate the SRL detection scheme. The pump beam is provided as an input pulse train 90, and the Stokes beam is provided as an input pulse train 92 that is modulated at high frequency $f$ (MHz). The output pulse train (shown at 94) includes a resulting amplitude modulation at the high frequency (MHz) due to stimulated Raman loss (SRL) that can only occur if both beams are present. This modulation of the originally non-modulated beam at the same frequency of the modulation f may then be detected by detection electronics and separate it from the laser noise that occurs at other frequencies. Stimulated Raman gain (SRG) of the Stokes-beam can be probed by modulating the pump beam and detecting the Stokes beam.

An SRL microscope may be provided with either or both forward and epi (reverse) detection. The Stokes beam may be modulated by an electro-optic (or acoustic-optic) modulator and then combined with the pump beam by a beam splitter/combiner. The collinear pump and Stokes beam are then positioned by an x-y scanner system, and directed toward a sample. The transmitted or reflected pump beam is filtered by a filter, and detected by a photodiode (PD). For epi detection, the back-scattered beams are collected by the excitation objective lens (OL) and separated from the excitation beams by a combination of a quarter wave plate ($\lambda/4$) and polarizing beam splitter (PBS). For forward detection, the forward-scattered beams are collected by a condenser. The SRL is measured by a lock-in amplifier to provide a pixel of the image. Three dimensional (3D) images are obtained by raster-scanning the laser focus across the sample by the scanner system and microspectroscopy can be performed by automated tuning of the pump wavelength.

Figure 11:
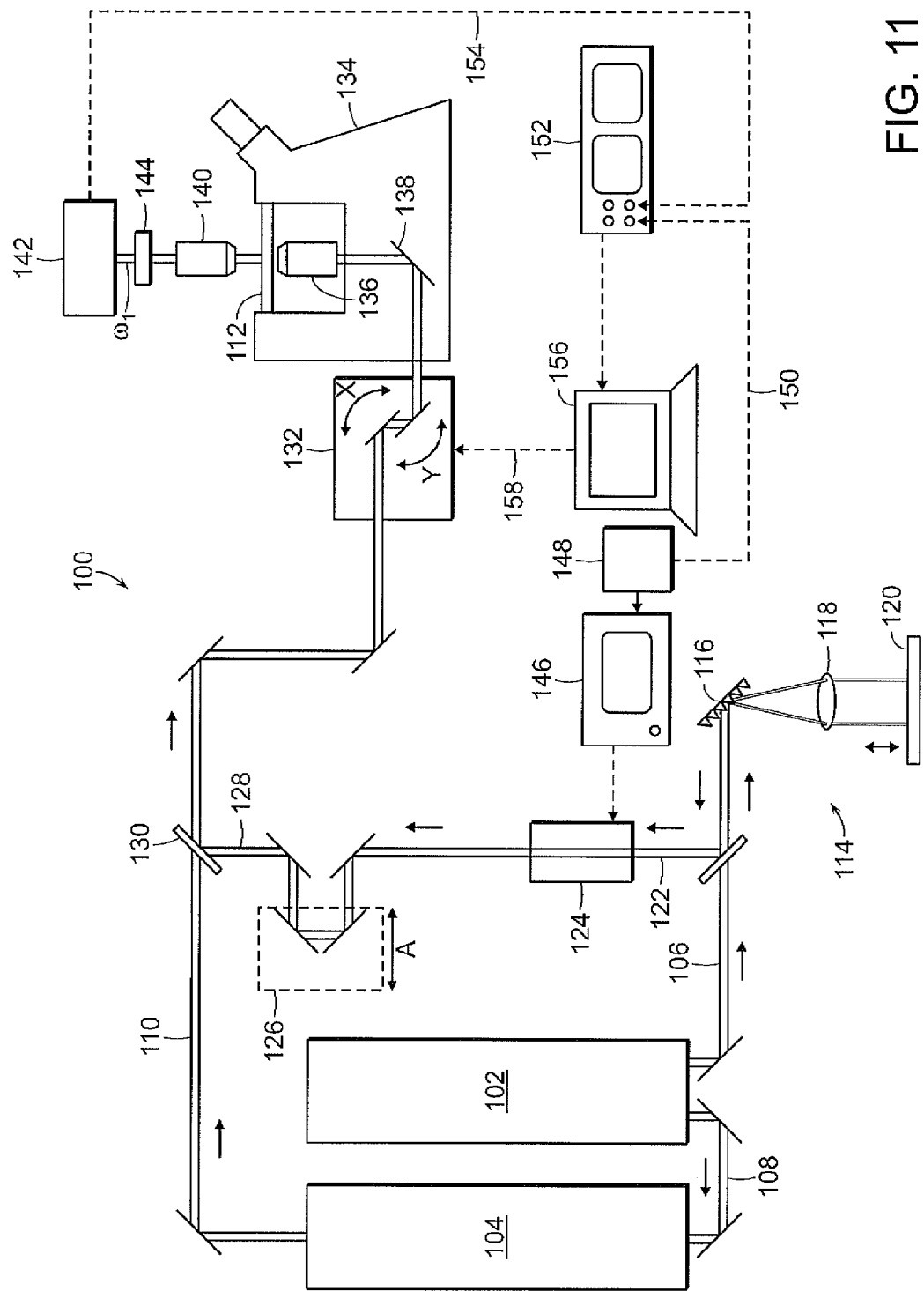
FIG. 11 shows an illustrative diagrammatic view of a microscopy imaging system in accordance with an embodiment of the invention.

In accordance with various embodiments, the microscopy system may be provided using a variety of sources and a variety of modulation techniques. FIG. 11, for example, shows a microscopy imaging system 100 in accordance with an embodiment of the invention that includes a dual frequency laser source 102 and an optical parametric oscillator 104. The dual frequency laser source 102 provides a broadband train of laser pulses 106 at a center frequency (e.g., including a Stokes frequency $\omega_1$ of, for example, 1064 nm), and a train of laser pulses 108 at a more narrow band of frequencies having a center frequency (e.g., 532 nm) to the optical parametric oscillator 104. The optical parametric oscillator may be, for example, as disclosed in U.S. Pat. No. 7,616,304, the disclosure of which is hereby incorporated by reference in its entirety. The output of the optical parametric oscillator provides a train of laser pulses 110 at a center frequency $\omega_2$ (e.g., a pump frequency) that is selected such that a difference between $\omega_1$ and $\omega_2$ (e.g., $\omega_p-\omega_S$) is resonant with a vibrational frequency of a sample 112 in a focal volume.

Each pulse of the train of laser pulses 106 is then spectrally shaped by a shaping assembly 114 that includes a dispersive element 116, a lens 118 and a spatial light modulator 120. The dispersive element 116 spectrally disperses each broadband pulse, and the spatial light modulator 120 then modulates different frequency components of the spectrally disperse broadband pulse to provide a train of shaped pulses 122.

The train of shaped laser pulses 122 is then modulated by a modulator 124, and is then phase adjusted at a translation stage 126 (that is adjustable as indicated at A) to ensure that the resulting train of modulated shaped laser pulses 128 and the train of laser pulses 110 at the center pump frequency are temporally overlapped. The two trains of laser pulses 128 and 110 are combined at a combiner 130 such that they are collinear and spatially overlapped as well.

The combined trains of laser pulses 128 and 110 are directed via a scan-head 132 (that scans in mutually orthogonal x and y directions), into a microscope 134 that includes optics 136 that direct and focus the combined trains of laser pulses 128 and 110 into the focal volume, e.g., via a mirror 138. The illumination from the focal volume is directed by a condenser 140 onto an optical detector 142 (e.g., a photodiode), and the modulated shaped beam (e.g., the Stokes beam) is blocked by an optical filter 144, such that the optical detector 142 measures the intensity of the other beam $\omega_1$ (e.g., the pump beam) only.

The train of shaped laser pulses 122 is modulated at modulation frequency $f$ (e.g., at least about 100 kHz), by a modulation system that includes, for example, the modulator 124, a controller 146 and a modulation source 148. The modulation source provides a common modulation control signal 150 to the controller 146 as well as to a signal processor 152. The integrated intensity of substantially all frequency components of the first pulse train 154 from the optical detector 142 is provided to the signal processor 152, and the intensity modulation due to the non-linear interaction of the train of laser pulses 128 with the train of laser pulses 110 in the focal volume is detected at the modulation frequency $f$ to provide a pixel of an image to a microscopy control computer 156. The microscopy control computer 156 is employed as an imaging system, and further provides user control of the scanhead 132 as shown at 158.

In accordance with an embodiment, the modulation system may provide amplitude modulation of the shaped pulses to provide the modulated shaped pulse train 128 such that only alternating pulses of the shaped pulse train 122 are coincident with the pulses of the $\omega_1$ pulse train 110. Such amplitude modulation of the shaped beam may be achieved using a Pockel cell and polarization analyzer as the modulator 124, and a Pockel cell driver as the controller 146. In accordance with another embodiment, the modulation rate is half the repetition rate of the laser such that every other pulse of the original $\omega_2$ pulse train is reduced in amplitude to provide that stimulated Raman scattering does not substantially occur in the focal volume with the pulses having the reduced amplitude. If the modulation rate is of the same order of the repetition rate of the laser, countdown electronics can be utilized to guarantee the synchronization (phase) between the modulation and the pulse train. Lower modulation rates are also possible, as long as the modulation frequency is faster that the laser noise. In further embodiments, the contrast pulses may have an amplitude that is substantially zero by switching off the pulses at the modulation frequency, for example using an electro-optic modulator or an acousto-optic modulator.

Amplitude modulation of the pump or Stokes pulse trains may therefore be achieved, and the increase of the Stokes pulse train or decrease of the pump pulse train may be measured. By modulating the pump train of pulses and then detecting the Stokes train of pulses from the focal volume, stimulated Raman gain (SRG) may be determined by the processing system. In further embodiments, the Stokes beam may be modulated, the pump beam may be detected from the focal volume, and stimulated Raman loss (SRL) may be determined by the processing system. In still further embodiments, the phase of one of both the shaped beam 122 and the non-shaped beam 110 may be phase modulated or frequency modulated as long as the modulation is done at the modulation frequency such that the detection system is able to extract the signal of interest. In still further embodiments, both the pump and Stokes beams may be modulation by a modulation system.

Systems of various embodiments of the invention, therefore, provide that stimulated Raman scattering microscopy may be achieved using a modulation of one of the pump or Stokes beams as a contrast mechanism. Stimulated Raman scattering microscopy bears most of the advantages of the existing methods. In particular, 1) it is a optically stimulated process which significantly enhances the molecular vibrational transition efficiency compared to conventional Raman microscopy which relies on spontaneous scattering; 2) it is a nonlinear process in which the signal is only generated at the microscopy objective focus, rendering a three-dimensional sectioning ability; 3) it only probes the vibrational resonance, and it is free from interference with the non-resonant background, unlike in the CARS microscopy where non-resonant background is always present; 4) the signal always scales linearly with the solute concentration, allowing ready analytical quantification; 5) the signal can be free from sample auto-fluorescence; 6) the phase matching condition is always satisfied for any relative orientations of the beams, unlike in the CARS microscopy; 7) visible and near-IR beams are used resulting in a higher penetration depth and spatial resolution than IR absorption microscopy; and 8) the detection of stimulated Raman gain or loss is also unaffected by ambient light, which permits such systems to be used in open environments.

The process may be viewed as a two photon process for excitation of a vibrational transition. The joint action of one photon annihilated from the pump beam and one photon created to the Stokes beam promotes the creation of the molecular vibrational phonon. The energy of the pump photon is precisely converted to the sum of the energy of the Stokes photon and the molecular vibrational phonon. As in any two photon optical process, the transition rate is proportional to the product of the pump beam intensity and the Stokes beam intensity. It is obvious that a molecular vibrational level is necessary for this process to happen, as required by the energy conservation. There is, therefore, no contribution from non-resonant background would be present. This represents a significant advantage over CARS microscopy which is severely limited by non-resonant background which not only distorts the spectrum but also carries unwanted laser noise.

The process may also be treated as a stimulated version of the spontaneous Raman scattering. In spontaneous Raman scattering, the Stokes photon mode is empty in the initial state and the vacuum field serves as the stimulated Stokes beam. That is why the efficiency is extremely low. The transition rate is only proportional to the pump beam intensity. In stimulated Raman scattering however, the Stokes photon mode has a large number of pre-occupied photons due to the presence of a strong laser beam, and the scattering process becomes stimulated in analogy to the stimulated emission. As a result, the transition rate is proportional not only to the pump beam intensity as in spontaneous Raman scattering, but also to the number of pre-occupied photons in Stokes photon mode which is again proportional to the Stokes beam intensity.

The process may also be accounted for as a heterodyne interference between the pump beam (or the Stokes beam) and a corresponding third-order nonlinear induced radiation at the same optical frequency as the pump beam (or the Stokes beam). These two third-order nonlinear induced polarizations for stimulated Raman gain and loss are different from each other, and are also distinct from the one responsible for CARS generation. If there are no additional electronic resonances involved, however, their absolute sizes are all the same.

For stimulated Raman loss of the pump beam, this third-order nonlinear induced polarization radiates at the pump beam frequency. The intensity dependence of this nonlinear radiation scales linearly with pump beam and quadratically with Stokes beam. Its final phase is 180 degree lag behind that of the input pump beam at the far field detector. Therefore, the interference between this nonlinear radiation and input pump beam results in an attenuation of the pump beam itself. And the intensity dependence of the interference term scales linearly with both the pump beam and Stokes beam.

For stimulated Raman gain for Stokes beam, a different third-order nonlinear induced polarization radiates at the Stokes beam frequency. The intensity dependence of this nonlinear radiation scales quadratically with pump beam and linearly with Stokes beam. Its final phase is the same as that of the input Stokes beam at the far field detector. Therefore, the interference between this nonlinear radiation and input Stokes beam results in an increase of the Stokes beam itself. The intensity dependence of the interference term again scales linearly with both the pump beam and Stokes beam.

Although the use of amplitude modulation has the highest modulation depth, this approach may introduce a linear background due to a modulation of the temperature or refractive index of the sample due to the intensity modulation on the sample. In accordance with another embodiment, the modulation system may provide polarization modulation, and may include a polarization device as the modulator, and a polarization controller as the controller. Every other pulse of the $\omega_2$ pulse train has a polarization that is different than that of the other preceding pulse. Each of the $\omega_r$ pulses of the pulse train is coincident with a $\omega_1$ pulse of the $\omega_1$ pulse train. Different modulation rates other than half of the repetition rate of the laser (in which every other pulse is different) can also be applied.

Polarization modulation also provides that stimulated Raman scattering does not substantially occur in the focal volume with the pulses having the altered unparallel polarization. In certain embodiments, the modulator includes a polarization filter to remove one of the sets of pulses as a further contrast mechanism. The polarization of the pulses may therefore, be modulated with respect to each other. In other embodiments, the detector itself may distinguish between the modulated pulses. In particular, when pump and Stokes pulse trains are perpendicular to each other, a different tensor element of the nonlinear susceptibility is probed compared to the case where pump and Stokes field are parallel. Different tensor elements have significantly different magnitudes. This converts the polarization modulation of the excitation beams into amplitude modulations of the gain/loss signal which can then be detected with the lock-in amplifier. Polarization modulation can be implemented with a Pockel cell. This approach has the advantage that it does not introduce a temperature modulation of the sample.

In accordance with other embodiments, one of the pulse trains may be modulated by time-shifting (or phase). For example, one pulse train may include alternating pulses that coincide with a $\omega_1$ pulse, while the remaining pulses are time shifted such that they do not coincide with a $\omega_1$ pulse. Modulation of one or both of the pump and Stokes beams may also be achieved by frequency modulation as disclosed for CARS microscopy, for example, in U.S. Pat. No. 7,352,458, the disclosure of which is hereby incorporated by reference in its entirety. In a frequency modulation system, the frequency of one or both of the pump and Stokes beams is alternately modulated at a modulation frequency such that a difference frequency between the pump and Stokes beams (e.g., $\omega_p - \omega_S$) is tuned in and out of a vibrational frequency of the sample. The detector then detects the gain/loss that is generated through non-linear interaction of $\omega_p$ and $\omega_S$ and the sample responsive to the modulation frequency. An output signal may be passed through a lock-in amplifier such that only changes at the time scale of the modulation period are provided in the final output. In accordance with further embodiments, other modulation schemes may be employed such as time-delay modulation, spatial beam mode modulation, etc., which will each introduce a modulation of a generated signal.

For example, in accordance with further embodiments, systems of the present invention may employ a dual frequency laser source, a first optical parametric oscillator, as well as an additional optical parametric oscillator that splits the power of the dual frequency laser source. The dual frequency laser source provides a first train of laser broadband pulses (including a pump frequency $\omega_1$) and a second train of laser pulses at a center frequency to the optical parametric oscillator and to the optical parametric oscillator. The first train of laser pulses are shaped as discussed above with reference to FIG. 11. The output of the optical parametric oscillator provides a third train of laser pulses at a center Stokes frequency $\omega_2$ that is selected such that a difference between $\omega_1$ and $\omega_2$ (e.g., $\omega_p \omega_S$) is resonant with a vibrational frequency of a sample (not shown) in a focal volume. The output of the optical parametric oscillator provides a fourth train of laser pulses at a center frequency $\omega_2'$ that is selected such that a difference between $\omega_1$ and $\omega_2$ (e.g., $\omega_p - \omega_S'$) is not resonant with a vibrational frequency of the sample in the focal volume.

The $\omega_2'$ pulses are passed through a half wave plate and combined with the $\omega_2$ pulses, which are passed through a different half wave plate. The half wave plates ensure that the pulse trains have different polarization such that one is transmitted by the beam splitter and the other is reflected. At this point, the combined pulse train includes both the $\omega_2$ and the $\omega_2'$ pulses, but with mutually orthogonal polarization. The combined $\omega_2$ and the $\omega_2'$ pulses are passed through a modulator that, responsive to a modulation signal that provides a modulation frequency $f$ from a modulation source. Based on the different polarization the modulator together with a polarization analyzer selects a different polarization at the modulation rate f, i.e., it selects $\omega_t$ or $\omega_2'$ pulses. The result is that a pulse train of alternating $\omega_2$ and $\omega_2'$ pulses is provided. The first shaped train of laser pulses and the alternating train of laser pulses and are combined at a combiner such that they are collinear and spatially overlapped as well, and the combined pulse trains are directed toward a sample as discussed above with reference to FIG. 11.

In accordance with further embodiments, the system may include an electronically locked laser such as an electronically locked mode-locked titanium sapphire laser in place of the optical parametric oscillator. In still further embodiments, the system may include a single optical parametric oscillator for providing both the $\omega_2$ and the $\omega_2'$ pulses, and the single optical parametric oscillator may provide the alternating train of laser pulses responsive to a modulation signal that is coupled to the signal processor. In accordance with further embodiments, the system may provide different spectral masks at different modulation frequencies, as well as multiple lock-in detectors tuned to the different modulation frequencies such that a plurality of species may be probed at the same time.

In still further embodiments, the microscopy imaging system may provide spectral-temporal excitation shaping in a CARS system. With reference again to FIG. 11, is such a CARS system, the shaped and modulated pump and/or Stokes trains of pulses 110, 128 are still directed toward the sample 112 in the focal volume, but the optical detector 142 and optical filter 144 are chosen such that the anti-Stokes pulses are received at the detector 142. In accordance with further embodiments, the optical detector 142 and filter 144 are selected such that two-color two-photon absorption is detected, or are chosen such that photo-thermal detection is provided.

Figure 12:
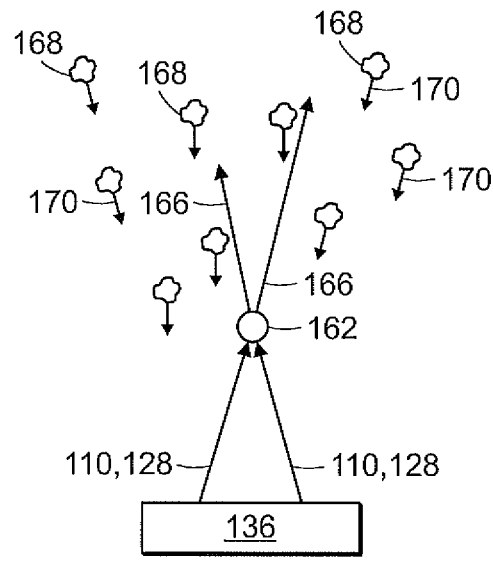
FIG. 12 shows an illustrative diagrammatic view of signal from a sample being reflected off of material within the sample volume in a system in accordance with an embodiment of the invention.

As shown in FIG. 12, during the non-linear interaction of the modulated Stokes train of pulses (shown diagrammatically at 128) and the pump train of laser pulses (shown diagrammatically at 110) when focused through optics 136 toward a focal area 162, both the pump and Stokes pulses are directed in a forward direction (as show diagrammatically at 166). A detector that is positioned forward of the sample will detect forward directed Stokes pulses that pass through the sample.

As also shown in FIG. 12, during the non-linear interaction of the shaped and modulated Stokes train of pulses 128 and the pump train of laser pulses 110 when focused through optics 136 toward the focal area generally shown at 162, some pump and Stokes pulses are initially forward directed (as shown diagrammatically at 166) but are then reflected by non-uniformities 168 within the sample (as show diagrammatically at 170) back toward the optics 136. In accordance with other embodiments therefore, a detector may also be positioned in the reverse direction with respect to the incoming pump and Stokes pulse trains that are directed into the focal volume. In such as reverse direction detection system, the detector will detect reflected pump pulses.

Figure 13:
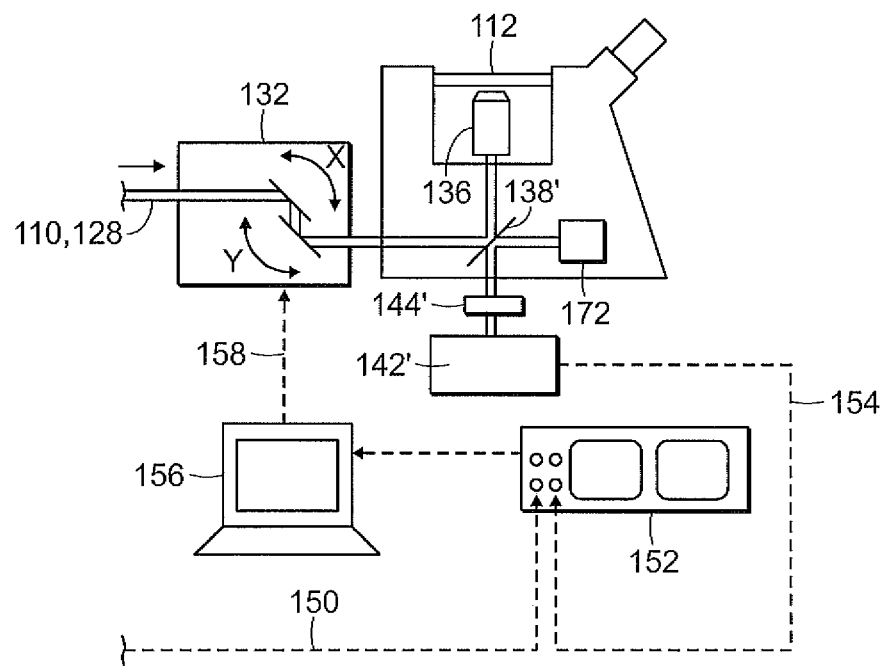
FIG. 13 shows an illustrative diagrammatic view of a portion of a stimulated Raman spectroscopy system in accordance with another embodiment of the invention employing epi-detection.

FIG. 13 shows a portion of system in accordance with a further embodiment of the invention in which system components having the same reference numerals as used in FIG. 11 (e.g., 110, 128, 112, 132, 136, 150, 152, 156, and 158) are the same as those in FIG. 11. The remaining elements from FIG. 11 not shown in FIG. 13 are the same, and the system may provide amplitude modulation, polarization modulation or frequency modulation as discussed above.

The system of FIG. 13, however, employs an optical detector 142' that receives via a filter 144' an integrated intensity of the optical frequency components of the train of Stokes pulses that are reflected through the common focal volume. In particular, the optics 136 directs and focuses the two trains of laser pulses into a sample 112 at the focal volume, and illumination that is directed in the epi-direction (by reflecting off other material in the sample following Raman scattering) is directed back through the optics 136 and beam splitter 138' onto the optical detector 142' via filter 144'. The image signal 154 is provided to the signal processing unit 152, which is in communication with the microscopy control computer 156 as discussed above with reference to FIG. 11.

As the signal and excitation beams have the same optical frequency, the system may provide that the beam splitter 138' is a 50/50 splitter that reflects 50% of an incident beam and transmits 50% of the incident beam through the beam splitter onto a heat absorber 172. This would ideally provide that 25% of the Stokes beam would be transmitted back into the detector 142'. In further embodiments, the beam splitter 138' may be a 20/80 splitter that reflects 20% of an incident beam and transmits 80% of the incident beam through the beam splitter, resulting in 4% signal on the detector 142'.

As with the embodiments discussed above, the system may provide modulation at a modulation frequency $f$, such as amplitude modulation, polarization modulation, phase modulation or frequency modulation, and the processor 152 detects a modulation (amplitude and/or phase) of the integrated intensity of substantially all of the optical frequency components of the Stokes pulse train due to the non-linear interaction of the Stokes pulse train with the pump pulse train within the common focal volume.

Figure 1:
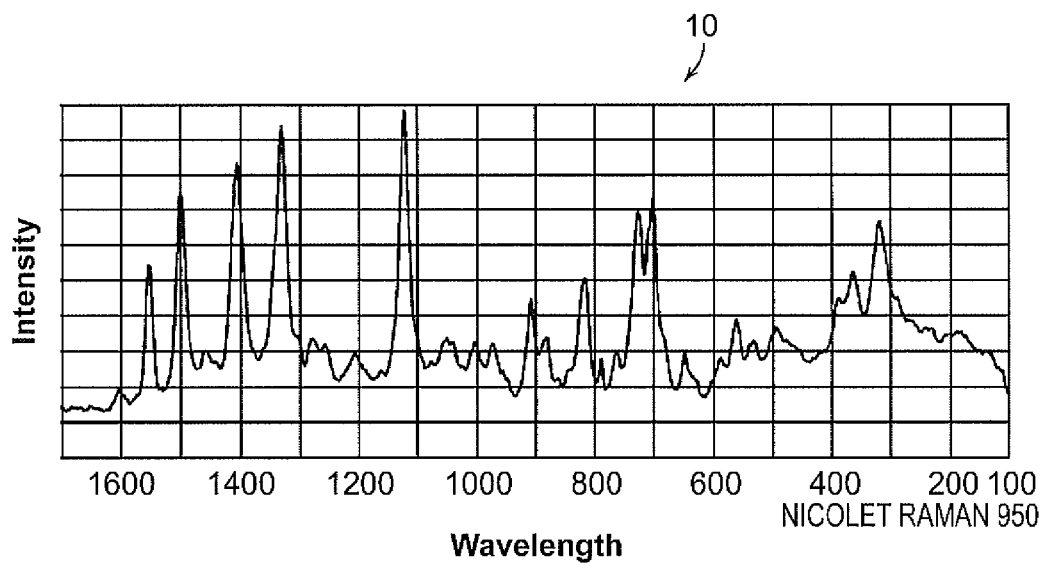
FIG. 1 shows an illustrative graphical representation of a Raman spectrum of the bioactive molecule adenosine triphosphate.
Figure 2:
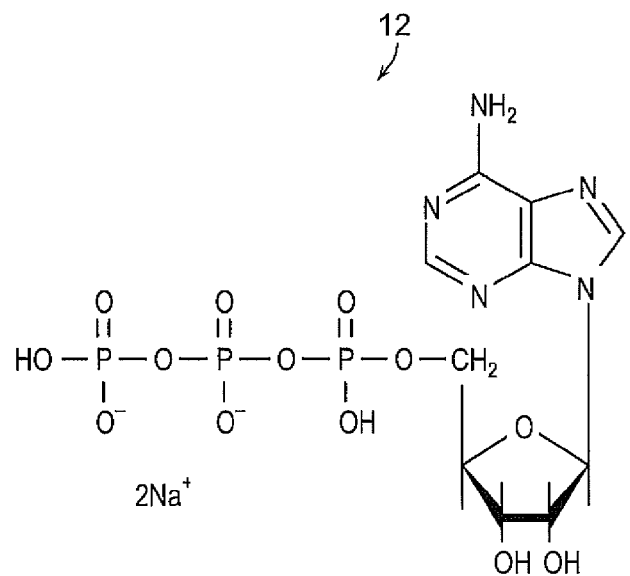
FIG. 2 shows an illustrative diagrammatic view of the molecule adenosine triphosphate.

The specificity of the SRS signal for a certain target species of the presented single-band approach with narrowband lasers is, however, limited, as different chemical bonds may have the same vibrational frequencies. The full specificity for Raman spectroscopy may be exploited only if the full vibrational spectrum of all bonds of a compound (e.g., as shown at 10 in FIG. 1) are probed rather than simply a single frequency.

In accordance with various embodiments of the invention therefore, spectral masks may be used to provide improved imaging. With reference for example, to the Raman spectrum shown at 10 in FIG. 1, none of the individual peaks is isolated from those other molecules, but the molecule's overall vibrational fingerprint, however, is unique. Complex molecules have several Raman active peaks, which combined result in a characteristic vibrational signature of the molecules. Vibrational spectra can thus be used as a label-free contrast mechanism for biomedical imaging.

Figure 14:
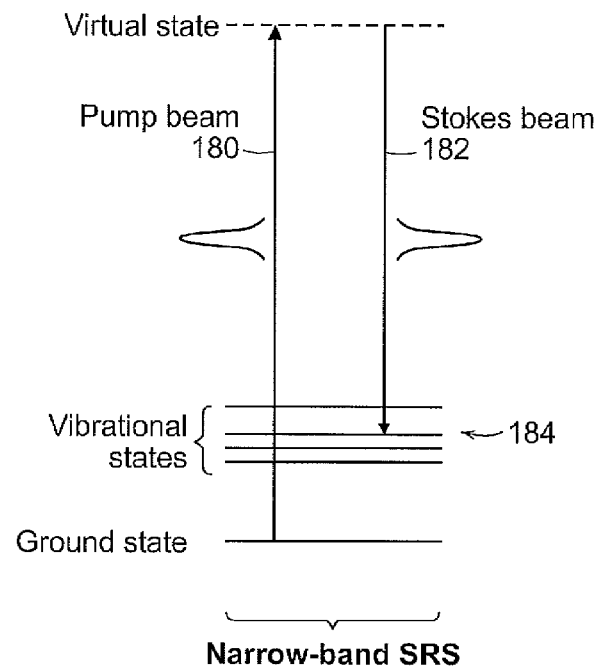
FIG. 14 shows an illustrative diagrammatic view of vibrational states of a narrow-band stimulated Raman spectroscopy system.

If only a single Raman peak is used as a marker-band, crosstalk between different compounds is possible. This can limit the specificity of the methods in many cases. It is possible to probe the a bigger portion Raman spectrum with SRS, by using at least one broadband laser source as pump- and Stokes beam. FIG. 14 shows an energy state diagram for narrow-band SRS using a narrow-band pump beam 180 and a narrow-band Stokes beam 182 wherein multiple vibration states exist as shown at 184. Every spectral component of the narrowband beam (frequency span is small than the width of the Raman line) experiences a gain or loss due to SRS, depending on whether the frequency difference of the center frequencies corresponds to a vibrational frequency of the molecules in the sample. The difference frequency is tuned into the resonance frequency of one oscillation of the target molecule. The other vibrational states are unaffected. As a result of the interaction with the sample, the pump-beam experiences a loss (SRL) and the Stokes beam a gain (SRG).

Figure 15:
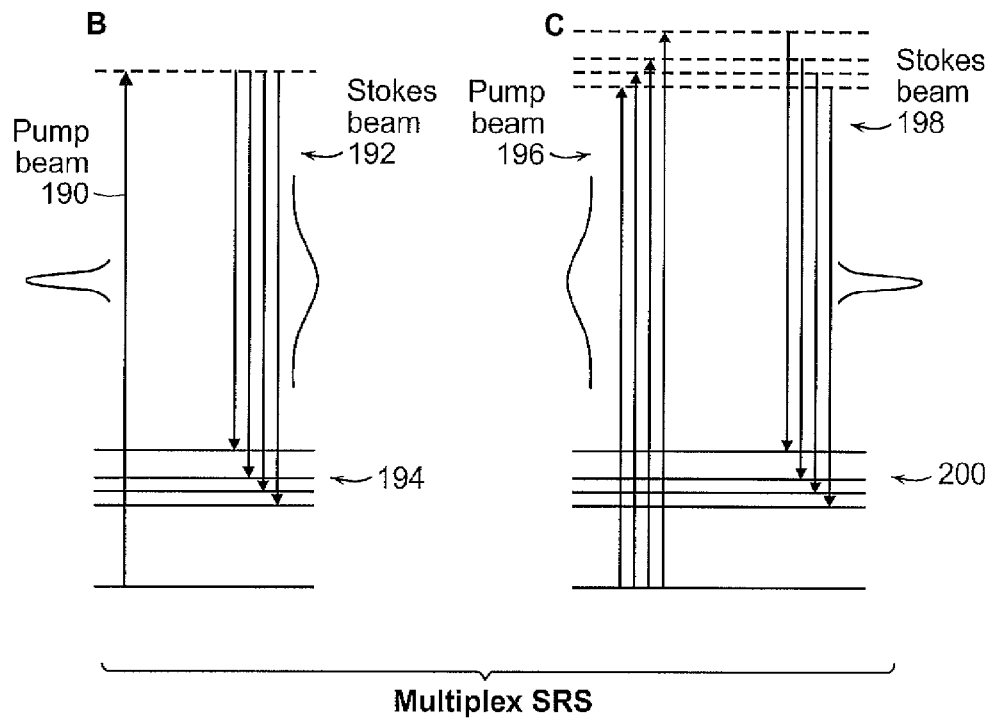
FIG. 15 show illustrative diagrammatic views of vibrational states in a multiplexed stimulated Raman spectroscopy system in accordance with an embodiment of the invention.

FIG. 15 shows two multiplex spectroscopy systems in which a narrow-band pump beam 190 is used with a broadband Stokes beam 192 to probe the vibrational states shown at 194. The individual components of broadband Stokes beam 192 and substantially all the frequency components of the narrowband pump beam 190 experience SRG or SRL respectively depending on whether the individual difference frequencies corresponds to on of the molecular vibrational states of the molecule 194.

In other embodiments as also shown in 15, a broadband pump beam 196 may be used with a narrow-band Stokes beam 198 to probe the vibrational states 200. The individual components of broadband pump beam 196 and substantially all the frequency components of the narrowband Stokes beam 198 experience SRL or SRG respectively depending on whether the individual difference frequencies corresponds to one of the molecular vibrational states of the molecule 200. Broadband excitation is also possible by two broadband pulse trains as pump and Stokes beams. The combination of all spectral components of both broadband beams contribute to the generation of the SRS signal.

As discussed with reference to FIG. 6 above, suppression of spectral cross-talk can be achieved by subtracting the signal from mask 2 (mainly containing the spectral components resonant with the interfering molecules) from the signal from mask 1 (mainly containing the spectral components resonant with the target molecules). As laser noise scales with the absolute signal, i.e., with the signal from the target component and the interfering species, the signal from the target molecules can easily be buried in the laser noise of the interfering species, when its concentration is much lower or the Raman scattering cross-section is much weaker. For this reason the subtraction from mask/and mask 2 has to be accomplished at a MHz rate since laser noise occurs mainly at lower frequencies. As such multivariate optical computation applied to excitation spectroscopy in SRS microscopy is equivalent to a complex frequency modulation scheme between two arbitrarily shaped excitation spectra.

Figure 16:
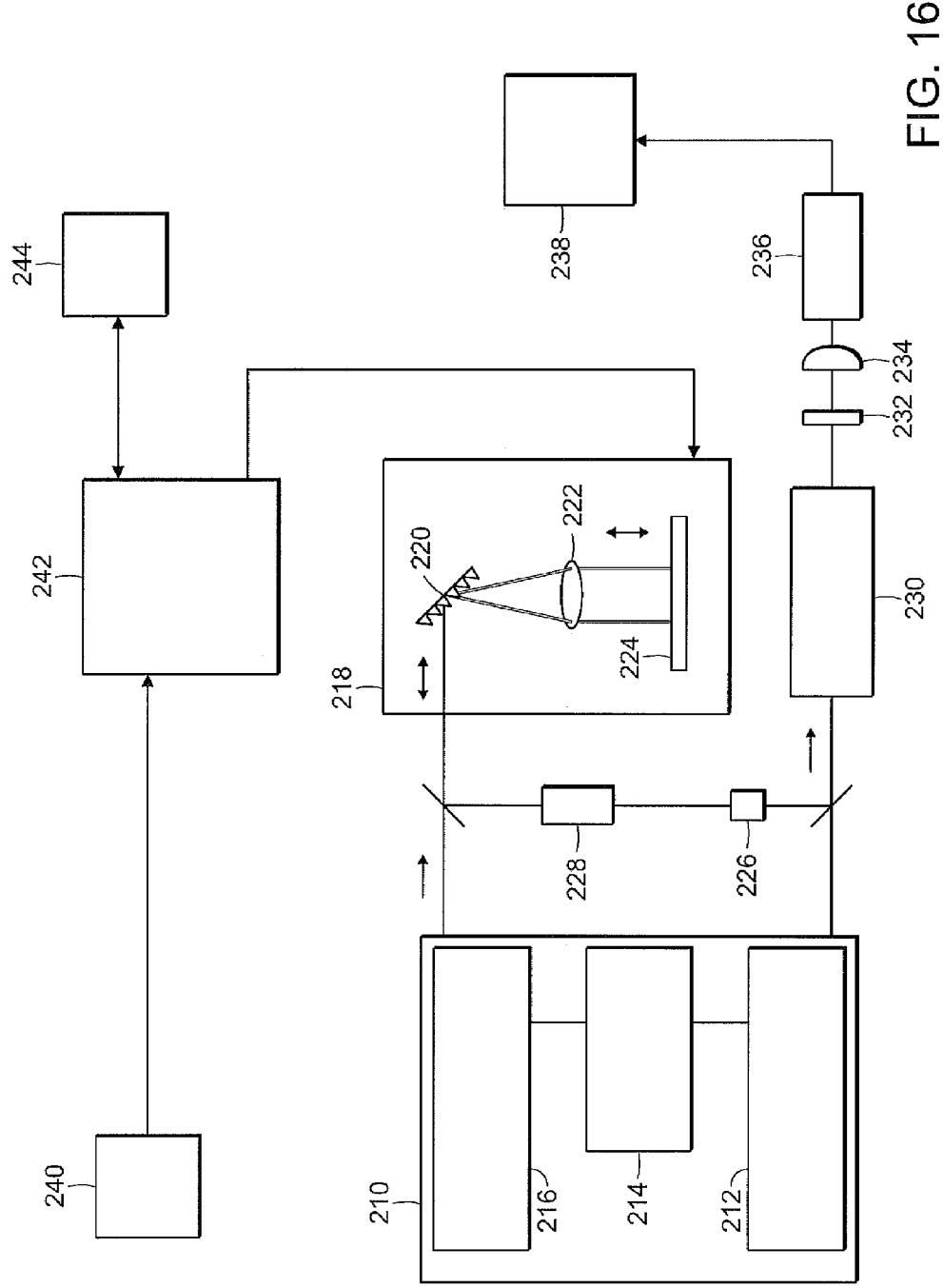
FIG. 16 shows an illustrative diagrammatic view of a microscopy imaging system in accordance with a further embodiment of the invention employing phase modulation.

FIG. 16 shows a high-frequency modulation system in accordance with another embodiment of the invention for multivariate optical computation in an SRS microscope. FIG. 16 shows a setup for a SRG microscope system with pixel-by-pixel mask subtraction. The system includes an illumination source system 210 that includes a picosecond (narrowband) optical parametric oscillator 212, an electronic synchronization unit 214, and a femtosecond (broadband) Ti:Sa laser 216. Excitation shaping is performed on the broad band pulse using a polarization pulse shaper 218 (containing a dispersive element such as a grating 220, an imaging lens 222 and a multiplex polarization shaper as a spatial light modulator 224).

The system also includes an analyzer 226 that only passes one polarization. A polarization modulator 228 (e.g., Pockel cell) is positioned in front of the analyzer and switches between which polarization is transmitted by the analyzer 226. As such it can switch between different spectral components of the broadband pulse depending whether the individual frequency components are set to be in the one or the other polarization state by the polarization pulse shaper. Electro-optical modulators such as Pockel cells allow switching at rates>1 MHz as desired. The shaped broadband pulse is overlapped with the narrowband Stokes pulse with a dichroic beam-combiner and aligned into a beam-scanning microscope 230. After passing or reflected through the focal volume of the focusing optics, the modulated pump beam is blocked by a filter 232 and the Stokes beam is detected with a photodetector such as a photodiode 234. The SRG on the originally non-modulated Stokes beam caused by the nonlinear interaction due to just the target molecule in the focus of the laser scanning microscope, can then be extracted with processing electronics such as a lock-in amplifier 236, detecting at the modulation rate of the electro-optic modulator. The lock-in amplifier takes the difference between the two spectra automatically. No additional modulation is necessary. A three-dimensional image of the distribution of just the target compound can then be acquired by scanning the focus through the sample.

As also shown in FIG. 16, the imaging system also includes an input device 240, a controller 242 that is coupled to a memory storage unit 244 and to the pulse-shaper 218. The signal processor 236 is also coupled to an output display device 238. A user may input at unit 240 an identification of an element to be analyzed, and the controller 242 may then obtain from a storage device 244 (e.g., via direct connection or via a network) the spectral shaping information associated with the element. The controller 242 then directs the modulator 218 to cause the desired modulation. In other embodiments, the user may input the pertinent spectral shaping information directly via the input unit 240.

Figure 17:
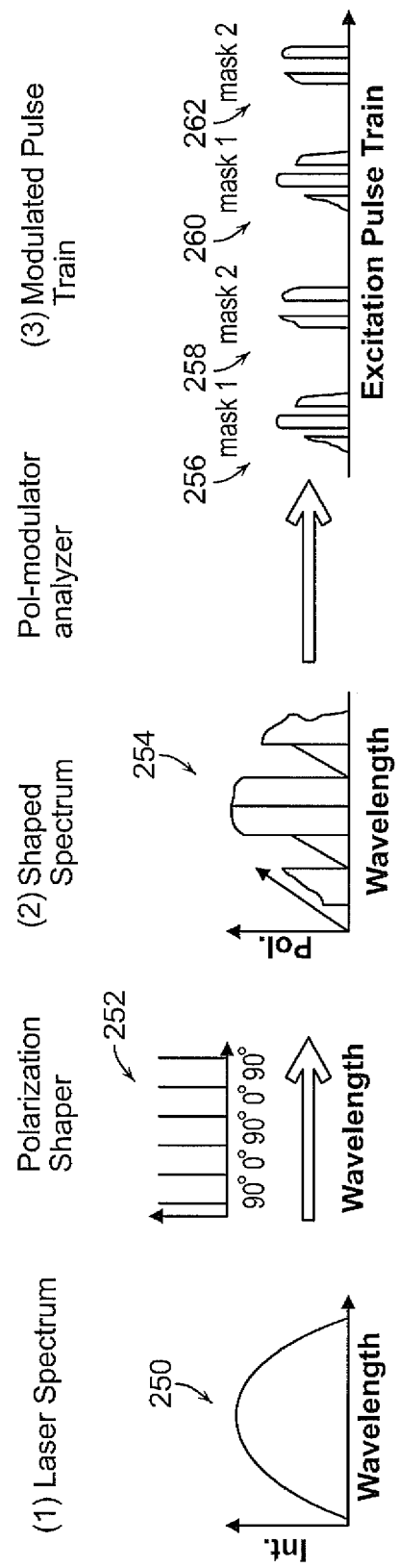
FIG. 17 shows an illustrative diagrammatic view of the generation of an excitation mask in accordance with a further embodiment of the invention.

FIG. 17 shows the modulation process between the two excitation masks in more details. The broad-band pulse 250 on the polarization pulse shaper is s-polarized (0°). After passing the pulse-shaper, the polarization of every spectral component can be adjusted to be anywhere between s (0°) and p (90°) as shown at 252. The analyzer after the electro-optic modulator is also set to s-polarization. Thus if the electro-optic modulator does not add any retardance, only the s-polarized portion of the shaped spectral components 254 are transmitted into the microscope.

When the modulator rotates the polarization of the transmitted beam by 90°, only the p-polarized portion of each spectral component (i.e., the complementary components of the broadband pulse) is transmitted into the microscope. It is therefore possible to switch between the selected excitation mask and it's complimentary at the rate of the electro-optic modulator. As shown at 256, 258, 260 and 262, alternating between the two masks provides a complex frequency modulation. Although FIG. 17 shows modulation rate half of the repetition rate of the laser. Also, FIG. 17 shows the possibility to select either s- or p-polarization only, any polarization setting possible. Additionally an amplitude-and-polarization-pulse-shaper can be used. This allows switching between two completely arbitrary masks, thus minimizing the power on the sample by blocking unneeded frequency components to generate the signal for the target molecule.

The described approach in FIGS. 16 and 17 shows how modulation phase can be utilized to detect the pure signal from one species in the presence of interfering species. The intensities of mask 1 and mask 2 are modulated exactly 180° out of phase with respect to each other, which the lock-in detector interprets as a negative sign and conducts the subtraction of the two masks. Generalizing this concept, two masks could be modulated 90° out of phase, which would allow separation of the two channels with a phase-sensitive detector such as a lock-in amplifier. This would allow simultaneous two-color imaging with a single lock-in amplifier, where mask 1 could be read from the x-channel and mask 2 from the y-channel. Alternatively two or even more masks may be modulated at different modulation frequencies and electronic processing units looking at these different rates could extract the individual spectral contributions of the different mask from the overall detected SRS or CARS from a single detector. In summary, spectral-temporal modulation of the broadband excitation beam, allows for encoding of the SRS signal in frequency-domain which can be analyzed electronically to isolate the individual spectral contributions.

Although the above discussion is directed to an application involving SRS microscopy, the ideas are valid for any type of contrast in microscopy that is based on excitation spectroscopy such as CARS, one- and two-photon absorption and emission, stimulated emission, photo-thermal scattering and photo-acoustic scattering.

It can also be applied to fast optical sensing (not necessarily microscopy) as needed in flow-cytometry. It is also possible to use a femtosecond-femtosecond configuration (i.e., both pump and Stokes beam are broadband), for which one or even both beams are shaped. The excitation masks are not as obvious in this situation, as all frequency combinations between the two pulses need to be considered, but they can be determined as the spectral resolution is solely determined by the spectral resolution of the pulse-shaper and not the bandwidth of the lasers.

The determination of the pulse shaping by the controller 242 follows the schemes of chemometrix. Again, with reference to FIG. 7, molecule A (shown at 75) is the analyte of interest, while elements B (shown at 76) and C (shown at 77) are the interferent species. Note that the corresponding known Raman spectra $\sigma(\Delta\omega)$ of A, B, and C are partially overlapping with each other as shown.

The objective is to design positive excitation spectral shapes. In a mixture of A, B and C with unknown concentrations c of each one, two positive excitation spectral shapes $I_+(\Delta\omega)$ and $I_-(\Delta\omega)$ (i.e. masks) may be designed such that the difference signal $\Delta S$ from these two excitation masks can selectively predict the concentration of molecule A without getting interference from molecules B and C. For a given excitation spectral shape $I(\Delta\omega)$, the obtained absorption signal S may be described as discussed above.

In accordance with certain embodiments, therefore, the spectral shaper (e.g., a spatial light modulator), may be set to provide a first mask having a first polarization at the same time that the spectral shaper is set to provide a second mask having a second polarization. The spectral shaper, therefore, provides two polarization distinct masks at the same time without changing. A polarization modulator may then switch between the two masks very quickly, permitting real-time subtraction of the results obtained using the second mask from the results obtained using the first mask.

It is also possible to use a femtosecond-femtosecond configuration (i.e., both pump and Stokes beam are broadband), for which one or even both beams are shaped, as the spectral resolution is solely determined by the spectral resolution of the pulse-shaper and not the bandwidth of the lasers. It can also be applied to fast optical sensing (not necessarily microscopy) as needed in flow-cytometry.

Figure 18B:
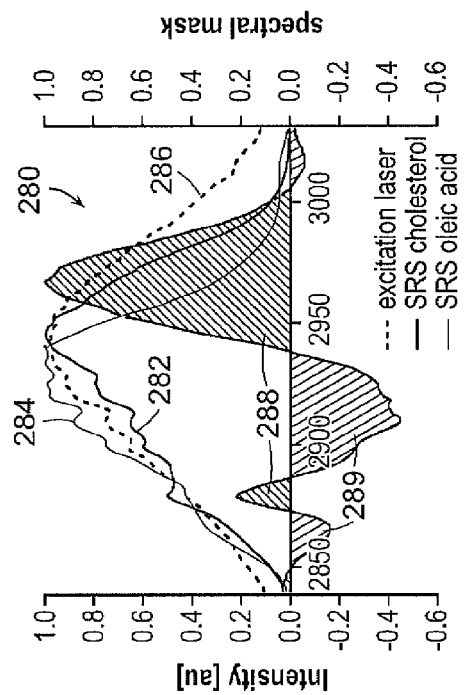
Figure 18D:
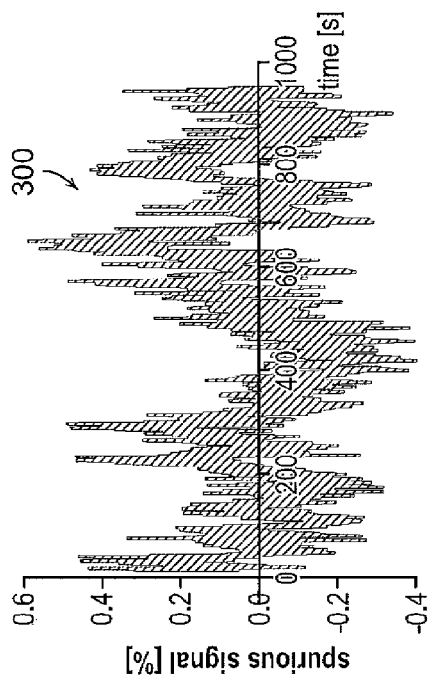
Figure 18A:
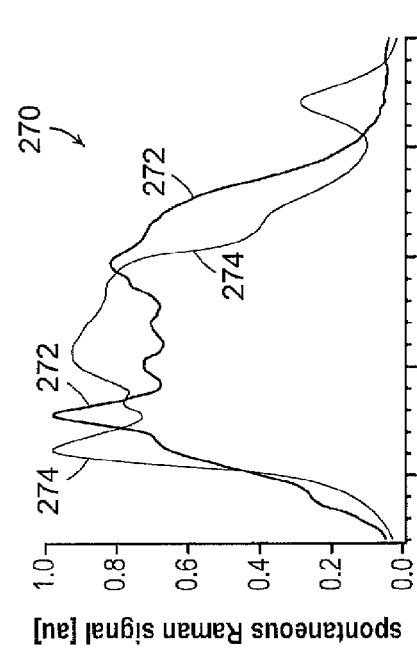

FIG. 18A shows at 270 the spontaneous Raman spectra of the two biochemicals cholesterol (shown at 272) and oleic acid (shown at 274) that have no isolated Raman vibrations but distinct Raman signatures. FIG. 18B shows at 280 the SRS spectra for cholesterol (shown at 282) and oleic acid (shown at 284) calculated for the laser excitation spectrum (shown at 286) measured by tuning a narrowband excitation mask across the broadband spectrum. The excitation mask specific for cholesterol that suppresses the interfering signal from oleic acid is generated automatically from the SRS spectra. Positive and negative spectral components are highlighted as shown at 288 and 289 respectively.

Figure 18C:
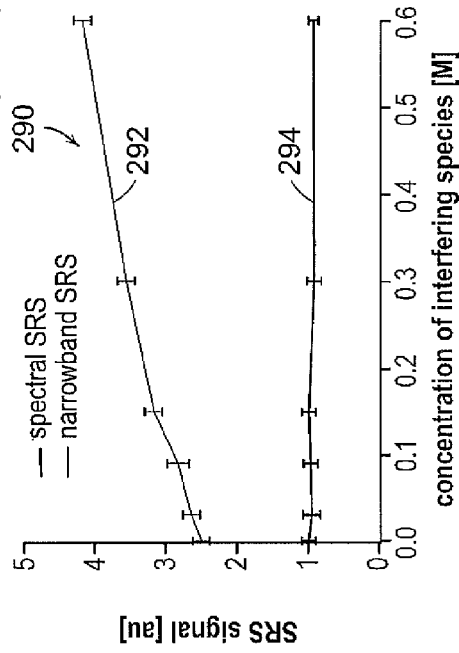

FIG. 18C shows at 290 a comparison of spectral and narrowband detection; the concentration of the interfering species (oleic acid) is increased, keeping the concentration of the target species (cholesterol) constant. While the narrowband SRS signal as shown at 292 falsely increases with increasing concentration of the interfering species, the spectral SRS signal as shown at 294 predicts the target concentration correctly independent of the concentration of the interferent and shows no increase.

Narrowband SRS imaging was achieved by applying a narrow-band mask to the broadband excitation around 2970 cm$^{-1}$. The suppression of the interfering signal may be quantified as follows. FIG. 18D shows at 300 the noise of a residual signal relative to the signal for unshaped excitation for oleic acid. FIGS. 18E-18G show at 310, 312 and 314 that spectral SRS imaging allows the suppression of interference from multiple chemical species. In particular, the images show the same area of a mixture containing protein extract, oleic acid and stearic acid taken for three excitation masks optimized for protein (shown at 310), oleic acid (shown at 312) and stearic acid (shown at 314). The imaging speed was 30 s per frame for a resolution of 512×512 pixels. The scale-bar is 25 μm.

FIGS. 19A-19H show data and images associated with the imaging of lipid storage in system of the multicellular organism *Caenorhabditis Elegans* (*C. Elegans*) obtained by a system in accordance with an embodiment of the invention. In particular, FIG. 19A shows at 320 an SRS spectrum of the biomolecules oleic acid (shown at 322), stearic acid (shown at 324) and protein (shown at 326) as computed from the spontaneous Raman library using the measured laser excitation spectrum (shown at 328).

FIG. 19B shows at 330 spectral masks computed from spectra at 320 and used for the imaging. In particular, FIG. 19B shows at 332 a mask for oleic acid, shows at 334 a mask for stearic acid, and shows at 336 a mask for protein. Spectral images taken from the same area in a section of a *C. Elegans* applying these spectral masks are shown in FIGS. 19C-19E for protein (shown at 340), oleic acid (shown at 342), and stearic acid (shown at 344). A comparison of the image for oleic acid (342) and stearic acid (344) shows that oleic and stearic acid depots co-localize and that there are no isolated depots of either one or the other. Also, comparison of oleic acid (342) and protein (340) shows that the lipid depots further localize with protein-dense organelles.

FIGS. 19F-19H also show spectral images of protein (shown at 346) and lipid distribution (shown at 348) as well as their overlay (shown at 350). The arrows shown in image 348 highlight both the sub-dermal and intestinal lipid storage depots. The imaging speed was 30 s per frame for a resolution of 512×512 pixels. The scale-bars are 25 μm.

FIGS. 20A-20L show the label-free microscopy of absorbing samples. In particular, FIG. 20A shows at 360 an energy diagram of stimulated Raman scattering (SRS) shown at 362 and two-color two-photon absorption (TPA) shown at 364. The TPA occurs as a background signal to SRS and vice versa. FIG. 20B shows at 370 excitation spectra, and in particular, shows excitation spectra of oleic acid (shown at 372) and a two-photon excitable sample (shown at 374) as determined from the laser excitation spectrum (shown at 374). FIG. 20C shows at 380 spectral masks used to acquire specific images of fat and two-photon excitable species. In particular, FIG. 20C shows at 382 a mask for fat, and shows at 384 a mask for the absorbing species.

FIGS. 20D-20F show spectral images of a chlorophyll rich algae sample. A Chlorophyll image (shown at 390) and lipid image (shown at 394) and their overlap (shown at 396) suggest that the lipid content of algae can be determined even in the presence of strongly absorbing (fluorescing) chlorophyll.

As shown in FIGS. 20G-20L, spectral images of two types of fat tissue (white fat shown at 396, 398, 400 and brown fat shown at 402, 404, 406) were acquired from fresh tissue, without any staining, fixing or sectioning. The TPA images (shown at 396 and 402) are dominated by hemoglobin absorption and show the microvasculature. The fat image (shown at 398 and 404) shows the different morphology of apidocytes in the different types of tissue. The image overlays (shown at 400 and 406) highlight that SRS and TPA are complementary techniques and can increase the information content of label-free microscopy. The imaging speed was 30 s per frame for a resolution of 512×512 pixels. The scale-bar is 25 μm.

Those skilled in the art will appreciate that numerous modifications and variations may be made to the above disclosed embodiments without departing from the spirit and scope of the claims.

The invention claimed is:

1. A microscopy imaging system comprising:
a light source system for providing a first train of pulses including a first broadband range of frequency components, and a second train of pulses including a second optical frequency such that a set of differences between the first broadband range of frequency components and the second optical frequency is resonant with a set of vibrational frequencies of a sample in the focal volume, wherein the second train of pulses is synchronized with the first train of pulses;
a spectral shaper including a dispersing element for spectrally dispersing frequency components of the broadband range of frequency components, spectrally modifying an optical property of at least some frequency components of the broadband range of frequency components, and spectrally combining using the dispersing element, the modified frequency components such that the broadband range of frequency components is shaped producing a shaped first train of pulses to specifically probe a spectral feature of interest from a sample, and to reduce information from features that are not of interest from the sample;
a modulator system for modulating a property of at least one of the shaped first train of pulses and the second train of pulses at a modulation frequency to provide a modulated train of pulses;
an optics system for directing and focusing the shaped first train of pulses and the second train of pulses as modulated toward a common focal volume;
an optical detector for detecting an integrated intensity of substantially all optical frequency components of a train of pulses of interest transmitted or reflected through the common focal volume; and
a processor for detecting a modulation at the modulation frequency of the integrated intensity of substantially all of the optical frequency components of the train of pulses of interest due to the non-linear interaction of the shaped first train of pulses with the second train of pulses as modulated in the common focal volume, and for providing an output signal for a pixel of an image for the microscopy imaging system;
wherein only one of the shaped train of laser pulses or the second train of pulses is modulated at the modulation frequency to provide the modulated train of pulses such that the other of the shaped train of laser pulses and the second train of pulses remains a non-modulated train of pulses;
wherein the optical detector detects the integrated intensity of substantially all optical frequency components of the non-modulated train of pulses transmitted or reflected through the common focal volume by blocking the modulated train of pulses; and
wherein the processor detects a modulation at the modulation frequency of the integrated intensity of substantially all of the optical frequency components of the non-modulated train of pulses due to the non-linear interaction of the modulated train of pulses with the non-modulated train of pulses in the common focal volume.

2. The microscopy imaging system as claimed in claim 1, wherein said optical property of either the shaped first train of pulses or the second train of pulses that is modulated is amplitude.

3. The microscopy imaging system as claimed in claim 1, wherein said optical property of either the shaped first train of pulses or the second train of pulses that is modulated is polarization and wherein said system further includes a polarization analyzer.

4. The microscopy imaging system as claimed in claim 1, wherein said spectral shaper and said modulator system are included in the same device.

5. The microscopy imaging system as claimed in claim 1 wherein said broadband range of frequency components includes a range of frequency components of at least 0.5 nm.

6. The microscopy imaging system as claimed in claim 1, wherein said broadband range of frequency components is discontinuous.

7. The microscopy imaging system as claimed in claim 1, wherein said second train of pulses also has a broadband range of frequency components.

8. The microscopy imaging system as claimed in claim 1, wherein the modulation frequency is at least 100kHz.

9. The microscopy imaging system as claimed in claim 1, wherein said imaging system employs stimulated Raman spectroscopy as a contrast mechanism, and wherein the first train of pulses provides a pump beam, and the second train of pulses is modulated by the modulator system at the modulation frequency to provide one of a pump beam and a Stokes beam such that a Raman loss is detected at the signal processor at the modulation frequency.

10. The microscopy imaging system as claimed in claim 1, wherein said imaging system employs stimulated Raman spectroscopy as a contrast mechanism, and wherein the first train of pulses provides a pump beam, and the second train of pulses is modulated by the modulator system at the modulation frequency to provide one of a pump beam and a Stokes beam such that a Raman gain is detected at the signal processor at the modulation frequency.

11. The microscopy imaging system as claimed in claim 1, wherein said modulation processor detects a modulation of the integrated intensity of substantially all of the optical frequency components of a train of anti-Stokes pulses due to the non-linear interaction of the shaped first train of pulses with the second train of pulses as modulated in the common focal volume.

12. The microscopy imaging system as claimed in claim 1, wherein said system employs two-photon absorption as a contrast mechanism in which one photon from the first train of pulses and a second photon from the second train of pulses are simultaneously absorbed.

13. The microscopy imaging system as claimed in claim 1, wherein said spectral shaper includes one of a spatial light modulator, a dazzler system, a multiplex electro-optic modulator, a multiplexed electro-acoustic modulator, or an acousto-optic tunable filter.

14. The microscopy imaging system as claimed in claim 1, wherein said spectral shaper differently modifies a polarization of different frequency components of the broadband range of frequency components of the first train of pulses.

15. The microscopy imaging system as claimed in claim 1, wherein said spectral shaper differently modifies an amplitude of different frequency components of the broadband range of frequency components of the first train of pulses.

16. The microscopy imaging system as claimed in claim 1, wherein said spectral shaper includes a spectral dispersion unit and a polarization spatial light modulator, and wherein said modulator is a polarization modulator, and wherein said system further includes a polarization analyzer that is positioned before or after the modulator.

17. A method of performing microscopy imaging using frequency modulation comprising the steps of:
providing a first train of pulses including a first broadband range of optical frequency components;
providing a second train of pulses including a second optical frequency such that a set of differences between the first broadband range of frequency components and the second optical frequency is resonant with a set of vibrational frequencies of a sample in the focal volume, wherein the second train of pulses is synchronized with the first train of pulses;
spectrally modifying an optical property of at least some frequency components of the first broadband range of frequency components to provide a shaped first train of pulses that is shaped to specifically probe a spectral feature of interest from a sample, and to reduce information from features that are not of interest from the sample, wherein each pulse of the shaped first train of pulses includes multiple frequency components that are differently modulated;
modulating an optical property of one of the shaped first train of pulses and the second train of pulses at a modulation frequency to provide a modulated train of pulses and providing the other of the shaped first train of pulses and the second train of pulses as a non-modulated train of pulses;
directing and focusing the modulated train of pulses and the non-modulated train of pulses toward a common focal volume;
detecting an integrated intensity of substantially all optical frequency components of the other of the modulated train of pulses and the non-modulated train of pulses transmitted or reflected through the common focal volume by blocking the modulated train of pulses;
detecting a modulation at the modulation frequency of the integrated intensity of substantially all of the optical frequency components of the non-modulated train of pulses due to the non-linear interaction of the modulated train of pulses with the non-modulated train of pulses in the common focal volume;
providing the detected modulation as the signal for a pixel of an image for a microscopy imaging system;
further spectrally modifying an optical property of at least further frequency components of the broadband range of frequency components of the first train of pulses to provide a further shaped first train of pulses to specifically probe a spectral feature from a sample that interferes with the spectral feature of interest from the sample;
subtracting the detected modulation of the integrated intensity of substantially all of the optical frequency components of the non-modulated train of pulses due to the non-linear interaction of the further shaped first train of pulses and the second train of pulses in the focal volume from the detected modulation of the integrated intensity of substantially all of the optical frequency components of non-modulated train of pulses due to the non-linear interaction of the originally shaped first train of pulses and the second train of pulses in the focal volume; and
providing the difference as the signal for a pixel of an image for the microscopy imaging system, wherein said step of further spectrally modifying an optical property of at least further frequency components of the broadband range of frequency components of the first train of pulses is performed for an entire scan area prior to the step of subtracting the detected modulation of the integrated intensity of substantially all of the optical frequency components obtained thereby from the detected modulation of the integrated intensity of substantially all of the optical frequency components of non-modulated train of pulses.

18. The method as claimed in claim 17, wherein said step of spectrally modifying an optical property of at least some frequency components and the step of modulating an optical property of one of the shaped first train of pulses and the second train of pulses to provide a modulated train of pulses is performed by the same device.

19. The method as claimed in claim 17, wherein said step of further spectrally modifying an optical property of at least further frequency components of the broadband range of frequency components of the first train of pulses and the step of subtracting the detected modulation of the integrated intensity of substantially all of the optical frequency components obtained thereby from the detected modulation of the integrated intensity of substantially all of the optical frequency components of non-modulated train of pulses are performed for one pixel prior to laser scanning to the next pixel.

20. The method as claimed in claim 17, wherein said step of spectrally modifying an optical property of at least some frequency components of the broadband range of frequency components of the shaped first train of pulses involves amplitude modulation.

21. The method as claimed in claim 17, wherein said step of spectrally modifying an optical property of at least some frequency components of the broadband range of frequency components of the shaped first train of pulses involves polarization modulation.

22. The method as claimed in claim 17, wherein said method includes the steps of providing different spectral masks at different modulation frequencies, as well as the steps of detecting multiple trains of pulses of interest using multiple lock-in detectors tuned to the different modulation frequencies such that a plurality of species may be probed at the same time.

23. A method of performing microscopy imaging comprising the steps of:
a) providing a first train of pulses at including a first broadband range of optical frequency components;
b) providing a second train of pulses including a second optical frequency such that a set of differences between the first broadband range of frequency components and the second frequency component is resonant with a set of vibrational frequencies of a sample in the focal volume, wherein the second train of pulses is synchronized with the first train of pulses;
c) spectrally modifying an optical property of at least some frequency components of the first broadband range of frequency components such that the first train of pulses is shaped to provide a shaped first train of pulses to specifically probe a spectral feature of interest from a sample, wherein each pulse of the shaped first train of pulses includes multiple frequency components that are differently modulated;
d) modulating a property of one of the shaped first train of pulses and the second train of pulses at a modulation frequency to provide a modulated train of pulses and to provide the other of the shaped first train of pulses and the second train of pulses as a non-modulated train of pulses;
e) directing and focusing the modulated train of pulses and the non-modulated train of pulses toward a common focal volume;
f) detecting an integrated intensity of substantially all optical frequency components of the non-modulated train of pulses at a modulation frequency transmitted or reflected through the common focal volume by blocking the modulated train of pulses;
g) detecting a modulation at the modulation frequency of the integrated intensity of substantially all of the modulated train of pulses due to the non-linear interaction of the modulated train of pulses with the non-modulated train of pulses in the common focal volume;
h) further spectrally modulating an optical property of at least some frequency components of the first broadband range of frequency components such that the first train of pulses is negatively shaped to provide to provide a negatively shaped first train of pulses to specifically probe a spectral feature from a sample that interferes with the spectral feature of interest from the sample, wherein each pulse of the negatively shaped first train of pulses includes multiple frequency components that are differently modulated;
i) modulating a property of one of the negatively shaped first train of pulses and the second train of pulses at a modulation frequency to provide a further modulated train of pulses to provide the other of the shaped first train of pulses and the second train of pulses as a non-further modulated train of pulses;
j) directing and focusing the further modulated train of pulses and non-further modulated train of pulses toward a common focal volume;
k) detecting a modulation of an integrated intensity of substantially all optical frequency components of non-further-modulated train of pulses and the further modulated train of pulses at a modulation frequency transmitted or reflected through the common focal volume by blocking the further modulated train of pulses;
l) subtracting the modulation of the integrated intensity of substantially all of the optical frequency components obtained from the modulation of the integrated intensity of substantially all of the further modulated train of pulses due to the non-linear interaction of the further modulated train of pulses and the non-further modulated train of pulses in the common focal volume to obtain a difference signal; and
m) providing an image for the microscopy imaging system responsive to the difference signal, wherein each of the steps a)-m) is performed for each pixel in a microscopy imaging system prior to each of the steps a)-m) being performed for another pixel.

24. A method of performing microscopy imaging using frequency modulation comprising the steps of:
providing a first train of pulses including a first broadband range of optical frequency components;
providing a second train of pulses including a second optical frequency such that a set of differences between the first broadband range of frequency components and the second optical frequency is resonant with a set of vibrational frequencies of a sample in the focal volume, wherein the second train of pulses is synchronized with the first train of pulses;
spectrally modifying an optical property of at least some frequency components of the first broadband range of frequency components to provide a shaped first train of pulses that is shaped to specifically probe a spectral feature of interest from a sample, and to reduce information from features that are not of interest from the sample, wherein each pulse of the shaped first train of pulses includes multiple frequency components that are differently modulated;

modulating an optical property of one of the shaped first train of pulses and the second train of pulses at a modulation frequency to provide a modulated train of pulses and providing the other of the shaped first train of pulses and the second train of pulses as a non-modulated train of pulses;

directing and focusing the modulated train of pulses and the non-modulated train of pulses toward a common focal volume;

detecting an integrated intensity of substantially all optical frequency components of the other of the modulated train of pulses and the non-modulated train of pulses transmitted or reflected through the common focal volume by blocking the modulated train of pulses;

detecting a modulation at the modulation frequency of the integrated intensity of substantially all of the optical frequency components of the non-modulated train of pulses due to the non-linear interaction of the modulated train of pulses with the non-modulated train of pulses in the common focal volume;

providing the detected modulation as the signal for a pixel of an image for a microscopy imaging system;

providing different spectral masks at different modulation frequencies; and detecting multiple trains of pulses of interest using multiple lock-in detectors tuned to the different modulation frequencies such that a plurality of species may be probed at the same time.

25. The method as claimed in claim 24, wherein said step of spectrally modifying an optical property of at least some frequency components and the step of modulating an optical property of one of the shaped first train of pulses and the second train of pulses to provide a modulated train of pulses is performed by the same device.

26. The method as claimed in claim 24, wherein said method further includes the steps of:

further spectrally modifying an optical property of at least further frequency components of the broadband range of frequency components of the first train of pulses to provide a further shaped first train of pulses to specifically probe a spectral feature from a sample that interferes with the spectral feature of interest from the sample;

subtracting the detected modulation of the integrated intensity of substantially all of the optical frequency components of the non-modulated train of pulses due to the non-linear interaction of the further shaped first train of pulses and the second train of pulses in the focal volume from the detected modulation of the integrated intensity of substantially all of the optical frequency components of non-modulated train of pulses due to the non-linear interaction of the originally shaped first train of pulses and the second train of pulses in the focal volume; and providing the difference as the signal for a pixel of an image for the microscopy imaging system.

27. The method as claimed in claim 26, wherein said step of further spectrally modifying an optical property of at least further frequency components of the broadband range of frequency components of the first train of pulses is performed for an entire scan area prior to the step of subtracting the detected modulation of the integrated intensity of substantially all of the optical frequency components obtained thereby from the detected modulation of the integrated intensity of substantially all of the optical frequency components of non-modulated train of pulses.

28. The method as claimed in claim 27, wherein said step of further spectrally modifying an optical property of at least further frequency components of the broadband range of frequency components of the first train of pulses and the step of subtracting the detected modulation of the integrated intensity of substantially all of the optical frequency components obtained thereby from the detected modulation of the integrated intensity of substantially all of the optical frequency components of non-modulated train of pulses are performed for one pixel prior to laser scanning to the next pixel.

29. The method as claimed in claim 24, wherein said step of spectrally modifying an optical property of at least some frequency components of the broadband range of frequency components of the shaped first train of pulses involves amplitude modulation.

30. The method as claimed in claim 24, wherein said step of spectrally modifying an optical property of at least some frequency components of the broadband range of frequency components of the shaped first train of pulses involves polarization modulation.

31. A method of performing microscopy imaging comprising the steps of:

a) providing a first train of pulses at including a first broadband range of optical frequency components;

b) providing a second train of pulses including a second optical frequency such that a set of differences between the first broadband range of frequency components and the second frequency component is resonant with a set of vibrational frequencies of a sample in the focal volume, wherein the second train of pulses is synchronized with the first train of pulses;

c) spectrally modifying an optical property of at least some frequency components of the first broadband range of frequency components such that the first train of pulses is shaped to provide a shaped first train of pulses to specifically probe a spectral feature of interest from a sample, wherein each pulse of the shaped first train of pulses includes multiple frequency components that are differently modulated;

d) modulating a property of one of the shaped first train of pulses and the second train of pulses at a modulation frequency to provide a modulated train of pulses and to provide the other of the shaped first train of pulses and the second train of pulses as a non-modulated train of pulses;

e) directing and focusing the modulated train of pulses and the non-modulated train of pulses toward a common focal volume;

f) detecting an integrated intensity of substantially all optical frequency components of the non-modulated train of pulses at a modulation frequency transmitted or reflected through the common focal volume by blocking the modulated train of pulses;

g) detecting a modulation at the modulation frequency of the integrated intensity of substantially all of the modulated train of pulses due to the non-linear interaction of the modulated train of pulses with the non-modulated train of pulses in the common focal volume;

h) further spectrally modulating an optical property of at least some frequency components of the first broadband range of frequency components such that the first train of pulses is negatively shaped to provide to provide a negatively shaped first train of pulses to specifically probe a spectral feature from a sample that interferes with the spectral feature of interest from the sample, wherein each pulse of the negatively shaped first train of pulses includes multiple frequency components that are differently modulated;

i) modulating a property of one of the negatively shaped first train of pulses and the second train of pulses at a modulation frequency to provide a further modulated train of pulses to provide the other of the shaped first train of pulses and the second train of pulses as a non-further modulated train of pulses;

j) directing and focusing the further modulated train of pulses and non-further modulated train of pulses toward a common focal volume;

k) detecting a modulation of an integrated intensity of substantially all optical frequency components of non-further-modulated train of pulses and the further modulated train of pulses at a modulation frequency transmitted or reflected through the common focal volume by blocking the further modulated train of pulses;

l) subtracting the modulation of the integrated intensity of substantially all of the optical frequency components obtained from the modulation of the integrated intensity of substantially all of the further modulated train of pulses due to the non-linear interaction of the further modulated train of pulses and the non-further modulated train of pulses in the common focal volume to obtain a difference signal; and m) providing an image for the microscopy imaging system responsive to the difference signal, wherein each of the steps a)-g) is performed for each pixel in a microscopy imaging system prior to each of the steps h)-m) being performed for each pixel.

* * * * *